US006309874B1

(12) United States Patent
Belusa

(10) Patent No.: US 6,309,874 B1
(45) Date of Patent: Oct. 30, 2001

(54) SELECTION MARKER

(75) Inventor: Roger Belusa, Lidingo (SE)

(73) Assignee: Karolinska Innovations AB, Stockholm (SE)

( * ) Notice: Subject to any disclaimer, the term of this patent is extended or adjusted under 35 U.S.C. 154(b) by 0 days.

(21) Appl. No.: 09/090,535

(22) Filed: Jun. 4, 1998

Related U.S. Application Data

(60) Provisional application No. 60/048,601, filed on Jun. 4, 1997.

(51) Int. Cl.[7] .................................................. C12N 15/55
(52) U.S. Cl. ................................. 435/252.3; 435/320.1; 435/195; 536/23.2
(58) Field of Search ............................... 435/195, 320.1, 435/252.3; 536/23.2

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,786,600 | 11/1988 | Kramer et al. | 435/235 |
| 4,800,159 | 1/1989 | Mullis et al. | 435/172.3 |
| 4,876,187 | 10/1989 | Duck et al. | 435/6 |
| 5,011,769 | 4/1991 | Duck et al. | 435/6 |

FOREIGN PATENT DOCUMENTS 0 068 763   1/1983   (EP) .

OTHER PUBLICATIONS

Kano, I., et al. (1989) FEBS Lett. 250(1), 91–98.*
Shull, G. E., et al. (1985) Nature 316, 691–695.*
Ovchinnikov, Y.U., et al. (1986) FEBS Lett. 201(2), 237–245.*
Shull, G. E., et al. (1986) Biochemistry 25(25), 8125–8132.*
Kawakami, K., et al. (1986) J. Biochem. 100, 389–397.*
A.K. Dudani et al., "Absence of gene amplification in human cell mutants resistant to cardiac glycosides", p. 27, Chemical Abstracts Pharmacology, vol. 108, No. 25 Jun. 20, 1988, abst. 108:215939X.
E.L. Burns et al., "Random mutagenesis of the sheep sodium–potassium–ATPase alpha–1 subunit generates a novel T797N mutation that results in a ouabain–resistant enzyme", p. 437, Chemical Abstracts Enzymes, vol. 119, No. 21, Nov. 22, 1993, abst. 119:220422e.
STN International, File Registry, Registry accession No. 168315–18–1, DNA (Chicken NA+/K+–ATPase .alpha.1–subunit gene 5'–regulatory regions, GenBank L43603.C1997.
E.L. Burns et al., "Random mutagenesis of the sheep Na, K–ATPase .alpha.1 subunit generating the ouabain–resistant mutant L793P", STN International, File Caplus No. 1996:412147, J. Biol Chem., vol. 271, No. 27, 1996.
V. Herrera et al., Three differentially expressed sodium–potassium ATPase .alpha. subunit isoforms: Structural and Functional Implications: S.TN International, File Caplus No. 1988:144404, J. Cell Biol., vol. 105, No. 4, 1987.

* cited by examiner

*Primary Examiner*—Charles L. Patterson, Jr.
(74) *Attorney, Agent, or Firm*—Young & Thompson

(57) ABSTRACT

The present invention relates to a new selection marker, namely a mutated (Na,K)-ATPase comprising the amino acid sequence:

IFIIANIPXPXGTVTIXXID wherein

X is chosen from the group of cysteine, leucine, glycine, alanine, valine, isoleucine, and where at least one X is cysteine.

7 Claims, 2 Drawing Sheets

Na+, K+ ATPase (NKA) activity in % in comparison with not treated

Ouabain concentration in μM

Leu799Cys NKA=Na+,K+-ATPase leucine 799 mutated to cysteine

WT NKA=natural NKA

SEQUENCE LISTING

```
<160> NUMBER OF SEQ ID NOS: 18

<210> SEQ ID NO 1
<211> LENGTH: 1212
<212> TYPE: PRT
<213> ORGANISM: Rattus rattus
<220> FEATURE:
<221> NAME/KEY: SITE
<222> LOCATION: (43)
<223> OTHER INFORMATION: Xaa is any amino acid.
<220> FEATURE:
<221> NAME/KEY: SITE
<222> LOCATION: (1103)
<223> OTHER INFORMATION: Xaa is any amino acid.

<400> SEQUENCE: 1

Gly Ala Ser Ala Gly Gly Gly Gly His Val Ala Ala Ala Ala Ala Ala
 1               5                  10                  15
```

```
Ala Ala Ala Ala Ala Ala Ala Ala Ser Val Arg Gly Ala Gly
            20                  25                  30

Arg Pro Pro Ser Phe Leu Arg Arg Gln Pro Xaa Phe Pro Pro Leu Gly
        35                  40                  45

Ser Pro Gly Ser Thr Leu Pro Ala Gly Ser Cys Ser Leu Leu Phe Leu
    50                  55                  60

Val Ser Ser His Arg Thr Arg Arg Gly Ala Arg Ser Ala Ala Thr Met
65                  70                  75                  80

Gly Lys Gly Val Gly Arg Asp Lys Tyr Glu Pro Ala Ala Val Ser Glu
                85                  90                  95

His Gly Asp Lys Lys Ser Lys Lys Ala Lys Lys Glu Arg Asp Met Asp
            100                 105                 110

Glu Leu Lys Lys Glu Val Ser Met Asp Asp His Lys Leu Ser Leu Asp
        115                 120                 125

Glu Leu His Arg Lys Tyr Gly Thr Asp Leu Ser Arg Gly Leu Thr Pro
    130                 135                 140

Ala Arg Ala Ala Glu Ile Leu Ala Arg Asp Gly Pro Asn Ala Leu Thr
145                 150                 155                 160

Pro Pro Pro Thr Thr Pro Glu Trp Val Lys Phe Cys Arg Gln Leu Phe
                165                 170                 175

Gly Gly Phe Ser Met Leu Leu Trp Ile Gly Ala Ile Leu Cys Phe Leu
            180                 185                 190

Ala Tyr Gly Ile Arg Ser Ala Thr Glu Glu Pro Pro Asn Asp Asp
        195                 200                 205

Leu Tyr Leu Gly Val Val Leu Ser Ala Val Ile Ile Thr Gly Cys
    210                 215                 220

Phe Ser Tyr Tyr Gln Glu Ala Lys Ser Ser Lys Ile Met Glu Ser Phe
225                 230                 235                 240

Lys Asn Met Val Pro Gln Gln Ala Leu Val Ile Arg Asn Gly Glu Lys
                245                 250                 255

Met Ser Ile Asn Ala Glu Asp Val Val Val Gly Asp Leu Val Glu Val
            260                 265                 270

Lys Gly Gly Asp Arg Ile Pro Ala Asp Leu Arg Ile Ile Ser Ala Asn
        275                 280                 285

Gly Cys Lys Val Asp Asn Ser Ser Leu Thr Gly Glu Ser Glu Pro Gln
    290                 295                 300

Thr Arg Ser Pro Asp Phe Thr Asn Glu Asn Pro Leu Glu Thr Arg Asn
305                 310                 315                 320

Ile Ala Phe Phe Ser Thr Asn Cys Val Glu Gly Thr Ala Arg Gly Ile
                325                 330                 335

Val Val Tyr Thr Gly Asp Arg Thr Val Met Gly Arg Ile Ala Thr Leu
            340                 345                 350

Ala Ser Gly Leu Glu Gly Gly Gln Thr Pro Ile Ala Glu Ile Glu
        355                 360                 365

His Phe Ile His Leu Ile Thr Gly Val Ala Val Phe Leu Gly Val Ser
    370                 375                 380

Phe Phe Ile Leu Ser Leu Ile Leu Glu Tyr Thr Trp Leu Glu Ala Val
385                 390                 395                 400

Ile Phe Leu Ile Gly Ile Ile Val Ala Asn Val Pro Glu Gly Leu Leu
                405                 410                 415

Ala Thr Val Thr Val Cys Leu Thr Leu Thr Ala Lys Arg Met Ala Arg
            420                 425                 430
```

-continued

```
Lys Asn Cys Leu Val Lys Asn Leu Glu Ala Val Glu Thr Leu Gly Ser
            435                 440                 445

Thr Ser Thr Ile Cys Ser Asp Lys Thr Gly Thr Leu Thr Gln Asn Arg
        450                 455                 460

Met Thr Val Ala His Met Trp Phe Asp Asn Gln Ile His Glu Ala Asp
465                 470                 475                 480

Thr Thr Glu Asn Gln Ser Gly Val Ser Phe Asp Lys Thr Ser Ala Thr
                485                 490                 495

Trp Phe Ala Leu Ser Arg Ile Ala Gly Leu Cys Asn Arg Ala Val Phe
                500                 505                 510

Gln Ala Asn Gln Glu Asn Leu Pro Ile Leu Lys Arg Ala Val Ala Gly
            515                 520                 525

Asp Ala Ser Glu Ser Ala Leu Leu Lys Cys Ile Glu Val Cys Cys Gly
        530                 535                 540

Ser Val Met Glu Met Arg Glu Lys Tyr Thr Lys Ile Val Glu Ile Pro
545                 550                 555                 560

Phe Asn Ser Thr Asn Lys Tyr Gln Leu Ser Ile His Lys Asn Pro Asn
                565                 570                 575

Ala Ser Glu Pro Lys His Leu Leu Val Met Lys Gly Ala Pro Glu Arg
            580                 585                 590

Ile Leu Asp Arg Cys Ser Ser Ile Leu Leu His Gly Lys Glu Gln Pro
        595                 600                 605

Leu Asp Glu Glu Leu Lys Asp Ala Phe Gln Asn Ala Tyr Leu Glu Leu
        610                 615                 620

Gly Gly Leu Gly Glu Arg Val Leu Gly Phe Cys His Leu Leu Leu Pro
625                 630                 635                 640

Asp Glu Gln Phe Pro Glu Gly Phe Gln Phe Asp Thr Asp Glu Val Asn
                645                 650                 655

Phe Pro Val Asp Asn Leu Cys Phe Val Gly Leu Ile Ser Met Ile Asp
            660                 665                 670

Pro Pro Arg Ala Ala Val Pro Asp Ala Val Gly Lys Cys Arg Ser Ala
        675                 680                 685

Gly Ile Lys Val Ile Met Val Thr Gly Asp His Pro Ile Thr Ala Lys
        690                 695                 700

Ala Ile Ala Lys Gly Val Gly Ile Ile Ser Glu Gly Asn Glu Thr Val
705                 710                 715                 720

Glu Asp Ile Ala Ala Arg Leu Asn Ile Pro Val Asn Gln Val Asn Pro
                725                 730                 735

Arg Asp Ala Lys Ala Cys Val Val His Gly Ser Asp Leu Lys Asp Met
            740                 745                 750

Thr Ser Glu Glu Leu Asp Asp Ile Leu Arg Tyr His Thr Glu Ile Val
        755                 760                 765

Phe Ala Arg Thr Ser Pro Gln Gln Lys Leu Ile Ile Val Glu Gly Cys
        770                 775                 780

Gln Arg Gln Gly Ala Ile Val Ala Val Thr Gly Asp Gly Val Asn Asp
785                 790                 795                 800

Ser Pro Ala Leu Lys Lys Ala Asp Ile Gly Val Ala Met Gly Ile Val
                805                 810                 815

Gly Ser Asp Val Ser Lys Gln Ala Ala Asp Met Ile Leu Leu Asp Asp
            820                 825                 830

Asn Phe Ala Ser Ile Val Thr Gly Val Glu Glu Gly Arg Leu Ile Phe
        835                 840                 845

Asp Asn Leu Lys Lys Ser Ile Ala Tyr Thr Leu Thr Ser Asn Ile Pro
```

-continued

```
                850             855             860
Glu Ile Thr Pro Phe Leu Ile Phe Ile Ile Ala Asn Ile Pro Cys Pro
865                 870             875             880
Leu Gly Thr Val Thr Ile Leu Cys Ile Asp Leu Gly Thr Asp Met Val
                885             890             895
Pro Ala Ile Ser Leu Ala Tyr Glu Gln Ala Glu Ser Asp Ile Met Lys
            900             905             910
Arg Gln Pro Arg Asn Pro Lys Thr Asp Lys Leu Val Asn Glu Arg Leu
        915             920             925
Ile Ser Met Ala Tyr Gly Gln Ile Gly Met Ile Gln Ala Leu Gly Gly
    930             935             940
Phe Phe Thr Tyr Phe Val Ile Leu Ala Glu Asn Gly Phe Leu Pro Phe
945             950             955             960
His Leu Leu Gly Ile Arg Glu Thr Trp Asp Asp Arg Trp Ile Asn Asp
                965             970             975
Val Glu Asp Ser Tyr Gly Gln Gln Trp Thr Tyr Glu Gln Arg Lys Ile
            980             985             990
Val Glu Phe Thr Cys His Thr Ala Phe Phe Val Ser Ile Val Val Val
        995             1000            1005
Gln Trp Ala Asp Leu Val Ile Cys Lys Thr Arg Arg Asn Ser Val Phe
    1010            1015            1020
Gln Gln Gly Met Lys Asn Lys Ile Leu Ile Phe Gly Leu Phe Glu Glu
1025            1030            1035            1040
Thr Ala Leu Ala Ala Phe Leu Ser Tyr Cys Pro Gly Met Gly Ala Ala
                1045            1050            1055
Leu Arg Met Tyr Pro Leu Lys Pro Thr Trp Trp Phe Cys Ala Phe Pro
            1060            1065            1070
Tyr Ser Leu Leu Ile Phe Val Tyr Asp Glu Val Arg Lys Leu Ile Ile
        1075            1080            1085
Arg Arg Arg Pro Gly Gly Trp Val Glu Lys Glu Thr Tyr Tyr Xaa Pro
    1090            1095            1100
Thr Ala Leu His Ala Val Glu His Cys Ala Thr His Cys Thr Tyr Pro
1105            1110            1115            1120
Tyr Pro Pro Phe Val Tyr Phe Lys Ser Trp Ser Ser Glu Leu Tyr Pro
                1125            1130            1135
Gly Arg Lys Ala Pro Lys His Val Gly Ile Gln Thr Ser Trp Asn Glu
            1140            1145            1150
Ala Cys Ser Cys Asn Gly Gly Arg Gly Glu Gly Cys Pro Lys Asn Thr
        1155            1160            1165
Val Asp Gly Asp Asp Ser Gly Glu Gly Leu Tyr Val Pro Phe Cys Phe
    1170            1175            1180
Cys Lys Lys Gly Lys Pro Gly Lys Thr Glu Arg Leu Arg Phe Ile Ser
1185            1190            1195            1200
Gly Phe Leu Gln Ile Lys Met Ala Ile Ile Thr Glu
                1205            1210
```

<210> SEQ ID NO 2
<211> LENGTH: 1212
<212> TYPE: PRT
<213> ORGANISM: Rattus rattus
<220> FEATURE:
<221> NAME/KEY: SITE
<222> LOCATION: (43)
<223> OTHER INFORMATION: Xaa is any amino acid.
<220> FEATURE:
<221> NAME/KEY: SITE
<222> LOCATION: (1103)
<223> OTHER INFORMATION: Xaa is any amino acid.

<400> SEQUENCE: 2

```
Gly Ala Ser Ala Gly Gly Gly His Val Ala Ala Ala Ala Ala
 1               5                  10                  15

Ala Ala Ala Ala Ala Ala Ala Ala Ser Val Arg Gly Ala Gly
            20                  25                  30

Arg Pro Pro Ser Phe Leu Arg Arg Gln Pro Xaa Phe Pro Pro Leu Gly
        35                  40                  45

Ser Pro Gly Ser Thr Leu Pro Ala Gly Ser Cys Ser Leu Leu Phe Leu
    50                  55                  60

Val Ser Ser His Arg Thr Arg Arg Gly Ala Arg Ser Ala Ala Thr Met
65                  70                  75                  80

Gly Lys Gly Val Gly Arg Asp Lys Tyr Glu Pro Ala Ala Val Ser Glu
                85                  90                  95

His Gly Asp Lys Lys Ser Lys Lys Ala Lys Lys Glu Arg Asp Met Asp
            100                 105                 110

Glu Leu Lys Lys Glu Val Ser Met Asp Asp His Lys Leu Ser Leu Asp
        115                 120                 125

Glu Leu His Arg Lys Tyr Gly Thr Asp Leu Ser Arg Gly Leu Thr Pro
    130                 135                 140

Ala Arg Ala Ala Glu Ile Leu Ala Arg Asp Gly Pro Asn Ala Leu Thr
145                 150                 155                 160

Pro Pro Pro Thr Thr Pro Glu Trp Val Lys Phe Cys Arg Gln Leu Phe
                165                 170                 175

Gly Gly Phe Ser Met Leu Leu Trp Ile Gly Ala Ile Leu Cys Phe Leu
            180                 185                 190

Ala Tyr Gly Ile Arg Ser Ala Thr Glu Glu Pro Pro Asn Asp Asp
        195                 200                 205

Leu Tyr Leu Gly Val Val Leu Ser Ala Val Val Ile Thr Gly Cys
    210                 215                 220

Phe Ser Tyr Tyr Gln Glu Ala Lys Ser Ser Lys Ile Met Glu Ser Phe
225                 230                 235                 240

Lys Asn Met Val Pro Gln Gln Ala Leu Val Ile Arg Asn Gly Glu Lys
                245                 250                 255

Met Ser Ile Asn Ala Glu Asp Val Val Val Gly Asp Leu Val Glu Val
            260                 265                 270

Lys Gly Gly Asp Arg Ile Pro Ala Asp Leu Arg Ile Ile Ser Ala Asn
        275                 280                 285

Gly Cys Lys Val Asp Asn Ser Ser Leu Thr Gly Glu Ser Glu Pro Gln
    290                 295                 300

Thr Arg Ser Pro Asp Phe Thr Asn Glu Asn Pro Leu Glu Thr Arg Asn
305                 310                 315                 320

Ile Ala Phe Phe Ser Thr Asn Cys Val Glu Gly Thr Ala Arg Gly Ile
                325                 330                 335

Val Val Tyr Thr Gly Asp Arg Thr Val Met Gly Arg Ile Ala Thr Leu
            340                 345                 350

Ala Ser Gly Leu Glu Gly Gly Gln Thr Pro Ile Ala Glu Glu Ile Glu
        355                 360                 365

His Phe Ile His Leu Ile Thr Gly Val Ala Val Phe Leu Gly Val Ser
    370                 375                 380

Phe Phe Ile Leu Ser Leu Ile Leu Glu Tyr Thr Trp Leu Glu Ala Val
385                 390                 395                 400
```

```
Ile Phe Leu Ile Gly Ile Ile Val Ala Asn Val Pro Glu Gly Leu Leu
                405                 410                 415
Ala Thr Val Thr Val Cys Leu Thr Leu Thr Ala Lys Arg Met Ala Arg
            420                 425                 430
Lys Asn Cys Leu Val Lys Asn Leu Glu Ala Val Glu Thr Leu Gly Ser
        435                 440                 445
Thr Ser Thr Ile Cys Ser Asp Lys Thr Gly Thr Leu Thr Gln Asn Arg
    450                 455                 460
Met Thr Val Ala His Met Trp Phe Asp Asn Gln Ile His Glu Ala Asp
465                 470                 475                 480
Thr Thr Glu Asn Gln Ser Gly Val Ser Phe Asp Lys Thr Ser Ala Thr
                485                 490                 495
Trp Phe Ala Leu Ser Arg Ile Ala Gly Leu Cys Asn Arg Ala Val Phe
            500                 505                 510
Gln Ala Asn Gln Glu Asn Leu Pro Ile Leu Lys Arg Ala Val Ala Gly
        515                 520                 525
Asp Ala Ser Glu Ser Ala Leu Leu Lys Cys Ile Glu Val Cys Cys Gly
    530                 535                 540
Ser Val Met Glu Met Arg Glu Lys Tyr Thr Lys Ile Val Glu Ile Pro
545                 550                 555                 560
Phe Asn Ser Thr Asn Lys Tyr Gln Leu Ser Ile His Lys Asn Pro Asn
                565                 570                 575
Ala Ser Glu Pro Lys His Leu Leu Val Met Lys Gly Ala Pro Glu Arg
            580                 585                 590
Ile Leu Asp Arg Cys Ser Ser Ile Leu Leu His Gly Lys Glu Gln Pro
        595                 600                 605
Leu Asp Glu Glu Leu Lys Asp Ala Phe Gln Asn Ala Tyr Leu Glu Leu
    610                 615                 620
Gly Gly Leu Gly Glu Arg Val Leu Gly Phe Cys His Leu Leu Leu Pro
625                 630                 635                 640
Asp Glu Gln Phe Pro Glu Gly Phe Gln Phe Asp Thr Asp Glu Val Asn
                645                 650                 655
Phe Pro Val Asp Asn Leu Cys Phe Val Gly Leu Ile Ser Met Ile Asp
            660                 665                 670
Pro Pro Arg Ala Ala Val Pro Asp Ala Val Gly Lys Cys Arg Ser Ala
        675                 680                 685
Gly Ile Lys Val Ile Met Val Thr Gly Asp His Pro Ile Thr Ala Lys
    690                 695                 700
Ala Ile Ala Lys Gly Val Gly Ile Ile Ser Glu Gly Asn Glu Thr Val
705                 710                 715                 720
Glu Asp Ile Ala Ala Arg Leu Asn Ile Pro Val Asn Gln Val Asn Pro
                725                 730                 735
Arg Asp Ala Lys Ala Cys Val Val His Gly Ser Asp Leu Lys Asp Met
            740                 745                 750
Thr Ser Glu Glu Leu Asp Asp Ile Leu Arg Tyr His Thr Glu Ile Val
        755                 760                 765
Phe Ala Arg Thr Ser Pro Gln Gln Lys Leu Ile Ile Val Glu Gly Cys
    770                 775                 780
Gln Arg Gln Gly Ala Ile Val Ala Val Thr Gly Asp Gly Val Asn Asp
785                 790                 795                 800
Ser Pro Ala Leu Lys Lys Ala Asp Ile Gly Val Ala Met Gly Ile Val
                805                 810                 815
```

-continued

Gly Ser Asp Val Ser Lys Gln Ala Ala Asp Met Ile Leu Leu Asp Asp
            820                 825                 830

Asn Phe Ala Ser Ile Val Thr Gly Val Glu Glu Gly Arg Leu Ile Phe
            835                 840                 845

Asp Asn Leu Lys Lys Ser Ile Ala Tyr Thr Leu Thr Ser Asn Ile Pro
850                 855                 860

Glu Ile Thr Pro Phe Leu Ile Phe Ile Ile Ala Asn Ile Pro Leu Pro
865                 870                 875                 880

Cys Gly Thr Val Thr Ile Leu Cys Ile Asp Leu Gly Thr Asp Met Val
                885                 890                 895

Pro Ala Ile Ser Leu Ala Tyr Glu Gln Ala Glu Ser Asp Ile Met Lys
            900                 905                 910

Arg Gln Pro Arg Asn Pro Lys Thr Asp Lys Leu Val Asn Glu Arg Leu
            915                 920                 925

Ile Ser Met Ala Tyr Gly Gln Ile Gly Met Ile Gln Ala Leu Gly Gly
            930                 935                 940

Phe Phe Thr Tyr Phe Val Ile Leu Ala Glu Asn Gly Phe Leu Pro Phe
945                 950                 955                 960

His Leu Leu Gly Ile Arg Glu Thr Trp Asp Asp Arg Trp Ile Asn Asp
                965                 970                 975

Val Glu Asp Ser Tyr Gly Gln Gln Trp Thr Tyr Glu Gln Arg Lys Ile
            980                 985                 990

Val Glu Phe Thr Cys His Thr Ala Phe Phe Val Ser Ile Val Val Val
            995                 1000                1005

Gln Trp Ala Asp Leu Val Ile Cys Lys Thr Arg Arg Asn Ser Val Phe
    1010                1015                1020

Gln Gln Gly Met Lys Asn Lys Ile Leu Ile Phe Gly Leu Phe Glu Glu
1025                1030                1035                1040

Thr Ala Leu Ala Ala Phe Leu Ser Tyr Cys Pro Gly Met Gly Ala Ala
                1045                1050                1055

Leu Arg Met Tyr Pro Leu Lys Pro Thr Trp Trp Phe Cys Ala Phe Pro
            1060                1065                1070

Tyr Ser Leu Leu Ile Phe Val Tyr Asp Glu Val Arg Lys Leu Ile Ile
            1075                1080                1085

Arg Arg Arg Pro Gly Gly Trp Val Glu Lys Glu Thr Tyr Tyr Xaa Pro
            1090                1095                1100

Thr Ala Leu His Ala Val Glu His Cys Ala Thr His Cys Thr Tyr Pro
1105                1110                1115                1120

Tyr Pro Pro Phe Val Tyr Phe Lys Ser Trp Ser Ser Glu Leu Tyr Pro
            1125                1130                1135

Gly Arg Lys Ala Pro Lys His Val Gly Ile Gln Thr Ser Trp Asn Glu
            1140                1145                1150

Ala Cys Ser Cys Asn Gly Gly Arg Gly Glu Gly Cys Pro Lys Asn Thr
            1155                1160                1165

Val Asp Gly Asp Asp Ser Gly Glu Gly Leu Tyr Val Pro Phe Cys Phe
            1170                1175                1180

Cys Lys Lys Gly Lys Pro Gly Lys Thr Glu Arg Leu Arg Phe Ile Ser
1185                1190                1195                1200

Gly Phe Leu Gln Ile Lys Met Ala Ile Ile Thr Glu
            1205                1210

<210> SEQ ID NO 3
<211> LENGTH: 1212
<212> TYPE: PRT

-continued

```
<213> ORGANISM: Rattus rattus
<220> FEATURE:
<221> NAME/KEY: SITE
<222> LOCATION: (43)
<223> OTHER INFORMATION: Xaa is any amino acid.
<220> FEATURE:
<221> NAME/KEY: SITE
<222> LOCATION: (1103)
<223> OTHER INFORMATION: Xaa is any amino acid.

<400> SEQUENCE: 3

Gly Ala Ser Ala Gly Gly Gly His Val Ala Ala Ala Ala Ala Ala
 1               5                  10                  15

Ala Ala Ala Ala Ala Ala Ala Ala Ala Ser Val Arg Gly Ala Gly
             20                  25                  30

Arg Pro Ser Phe Leu Arg Arg Gln Pro Xaa Phe Pro Pro Leu Gly
         35                  40                  45

Ser Pro Gly Ser Thr Leu Pro Ala Gly Ser Cys Ser Leu Leu Phe Leu
     50                  55                  60

Val Ser Ser His Arg Thr Arg Arg Gly Ala Arg Ser Ala Ala Thr Met
 65                  70                  75                  80

Gly Lys Gly Val Gly Arg Asp Lys Tyr Glu Pro Ala Ala Val Ser Glu
                 85                  90                  95

His Gly Asp Lys Lys Ser Lys Lys Ala Lys Lys Glu Arg Asp Met Asp
            100                 105                 110

Glu Leu Lys Lys Glu Val Ser Met Asp Asp His Lys Leu Ser Leu Asp
        115                 120                 125

Glu Leu His Arg Lys Tyr Gly Thr Asp Leu Ser Arg Gly Leu Thr Pro
    130                 135                 140

Ala Arg Ala Ala Glu Ile Leu Ala Arg Asp Gly Pro Asn Ala Leu Thr
145                 150                 155                 160

Pro Pro Pro Thr Thr Pro Glu Trp Val Lys Phe Cys Arg Gln Leu Phe
                165                 170                 175

Gly Gly Phe Ser Met Leu Leu Trp Ile Gly Ala Ile Leu Cys Phe Leu
            180                 185                 190

Ala Tyr Gly Ile Arg Ser Ala Thr Glu Glu Pro Pro Asn Asp Asp
        195                 200                 205

Leu Tyr Leu Gly Val Val Leu Ser Ala Val Val Ile Ile Thr Gly Cys
    210                 215                 220

Phe Ser Tyr Tyr Gln Glu Ala Lys Ser Ser Lys Ile Met Glu Ser Phe
225                 230                 235                 240

Lys Asn Met Val Pro Gln Gln Ala Leu Val Ile Arg Asn Gly Glu Lys
                245                 250                 255

Met Ser Ile Asn Ala Glu Asp Val Val Gly Asp Leu Val Glu Val
            260                 265                 270

Lys Gly Gly Asp Arg Ile Pro Ala Asp Leu Arg Ile Ile Ser Ala Asn
        275                 280                 285

Gly Cys Lys Val Asp Asn Ser Ser Leu Thr Gly Glu Ser Glu Pro Gln
    290                 295                 300

Thr Arg Ser Pro Asp Phe Thr Asn Glu Asn Pro Leu Glu Thr Arg Asn
305                 310                 315                 320

Ile Ala Phe Phe Ser Thr Asn Cys Val Glu Gly Thr Ala Arg Gly Ile
                325                 330                 335

Val Val Tyr Thr Gly Asp Arg Thr Val Met Gly Arg Ile Ala Thr Leu
            340                 345                 350

Ala Ser Gly Leu Glu Gly Gly Gln Thr Pro Ile Ala Glu Glu Ile Glu
```

-continued

```
            355                 360                 365
His Phe Ile His Leu Ile Thr Gly Val Ala Val Phe Leu Gly Val Ser
    370                 375                 380

Phe Phe Ile Leu Ser Leu Ile Leu Glu Tyr Thr Trp Leu Glu Ala Val
385                 390                 395                 400

Ile Phe Leu Ile Gly Ile Ile Val Ala Asn Val Pro Glu Gly Leu Leu
                405                 410                 415

Ala Thr Val Thr Val Cys Leu Thr Leu Thr Ala Lys Arg Met Ala Arg
                420                 425                 430

Lys Asn Cys Leu Val Lys Asn Leu Glu Ala Val Glu Thr Leu Gly Ser
        435                 440                 445

Thr Ser Thr Ile Cys Ser Asp Lys Thr Gly Thr Leu Thr Gln Asn Arg
    450                 455                 460

Met Thr Val Ala His Met Trp Phe Asp Asn Gln Ile His Glu Ala Asp
465                 470                 475                 480

Thr Thr Glu Asn Gln Ser Gly Val Ser Phe Asp Lys Thr Ser Ala Thr
                485                 490                 495

Trp Phe Ala Leu Ser Arg Ile Ala Gly Leu Cys Asn Arg Ala Val Phe
                500                 505                 510

Gln Ala Asn Gln Glu Asn Leu Pro Ile Leu Lys Arg Ala Val Ala Gly
        515                 520                 525

Asp Ala Ser Glu Ser Ala Leu Leu Lys Cys Ile Glu Val Cys Cys Gly
    530                 535                 540

Ser Val Met Glu Met Arg Glu Lys Tyr Thr Lys Ile Val Glu Ile Pro
545                 550                 555                 560

Phe Asn Ser Thr Asn Lys Tyr Gln Leu Ser Ile His Lys Asn Pro Asn
                565                 570                 575

Ala Ser Glu Pro Lys His Leu Leu Val Met Lys Gly Ala Pro Glu Arg
                580                 585                 590

Ile Leu Asp Arg Cys Ser Ser Ile Leu Leu His Gly Lys Glu Gln Pro
                595                 600                 605

Leu Asp Glu Glu Leu Lys Asp Ala Phe Gln Asn Ala Tyr Leu Glu Leu
        610                 615                 620

Gly Gly Leu Gly Glu Arg Val Leu Gly Phe Cys His Leu Leu Leu Pro
625                 630                 635                 640

Asp Glu Gln Phe Pro Glu Gly Phe Gln Phe Asp Thr Asp Glu Val Asn
                645                 650                 655

Phe Pro Val Asp Asn Leu Cys Phe Val Gly Leu Ile Ser Met Ile Asp
                660                 665                 670

Pro Pro Arg Ala Ala Val Pro Asp Ala Val Gly Lys Cys Arg Ser Ala
                675                 680                 685

Gly Ile Lys Val Ile Met Val Thr Gly Asp His Pro Ile Thr Ala Lys
    690                 695                 700

Ala Ile Ala Lys Gly Val Gly Ile Ile Ser Glu Gly Asn Glu Thr Val
705                 710                 715                 720

Glu Asp Ile Ala Ala Arg Leu Asn Ile Pro Val Asn Gln Val Asn Pro
                725                 730                 735

Arg Asp Ala Lys Ala Cys Val Val His Gly Ser Asp Leu Lys Asp Met
                740                 745                 750

Thr Ser Glu Glu Leu Asp Asp Ile Leu Arg Tyr His Thr Glu Ile Val
        755                 760                 765

Phe Ala Arg Thr Ser Pro Gln Gln Lys Leu Ile Ile Val Glu Gly Cys
    770                 775                 780
```

-continued

```
Gln Arg Gln Gly Ala Ile Val Ala Val Thr Gly Asp Gly Val Asn Asp
785                 790                 795                 800

Ser Pro Ala Leu Lys Lys Ala Asp Ile Gly Val Ala Met Gly Ile Val
                805                 810                 815

Gly Ser Asp Val Ser Lys Gln Ala Ala Asp Met Ile Leu Leu Asp Asp
            820                 825                 830

Asn Phe Ala Ser Ile Val Thr Gly Val Glu Glu Gly Arg Leu Ile Phe
        835                 840                 845

Asp Asn Leu Lys Lys Ser Ile Ala Tyr Thr Leu Thr Ser Asn Ile Pro
    850                 855                 860

Glu Ile Thr Pro Phe Leu Ile Phe Ile Ile Ala Asn Ile Pro Cys Pro
865                 870                 875                 880

Cys Gly Thr Val Thr Ile Leu Cys Ile Asp Leu Gly Thr Asp Met Val
                885                 890                 895

Pro Ala Ile Ser Leu Ala Tyr Glu Gln Ala Glu Ser Asp Ile Met Lys
            900                 905                 910

Arg Gln Pro Arg Asn Pro Lys Thr Asp Lys Leu Val Asn Glu Arg Leu
        915                 920                 925

Ile Ser Met Ala Tyr Gly Gln Ile Gly Met Ile Gln Ala Leu Gly Gly
    930                 935                 940

Phe Phe Thr Tyr Phe Val Ile Leu Ala Glu Asn Gly Phe Leu Pro Phe
945                 950                 955                 960

His Leu Leu Gly Ile Arg Glu Thr Trp Asp Asp Arg Trp Ile Asn Asp
                965                 970                 975

Val Glu Asp Ser Tyr Gly Gln Gln Trp Thr Tyr Glu Gln Arg Lys Ile
            980                 985                 990

Val Glu Phe Thr Cys His Thr Ala Phe Phe Val Ser Ile Val Val Val
        995                 1000                1005

Gln Trp Ala Asp Leu Val Ile Cys Lys Thr Arg Arg Asn Ser Val Phe
    1010                1015                1020

Gln Gln Gly Met Lys Asn Lys Ile Leu Ile Phe Gly Leu Phe Glu Glu
1025                1030                1035                1040

Thr Ala Leu Ala Ala Phe Leu Ser Tyr Cys Pro Gly Met Gly Ala Ala
                1045                1050                1055

Leu Arg Met Tyr Pro Leu Lys Pro Thr Trp Trp Phe Cys Ala Phe Pro
            1060                1065                1070

Tyr Ser Leu Leu Ile Phe Val Tyr Asp Glu Val Arg Lys Leu Ile Ile
        1075                1080                1085

Arg Arg Arg Pro Gly Gly Trp Val Glu Lys Glu Thr Tyr Tyr Xaa Pro
    1090                1095                1100

Thr Ala Leu His Ala Val Glu His Cys Ala Thr His Cys Thr Tyr Pro
1105                1110                1115                1120

Tyr Pro Pro Phe Val Tyr Phe Lys Ser Trp Ser Ser Glu Leu Tyr Pro
                1125                1130                1135

Gly Arg Lys Ala Pro Lys His Val Gly Ile Gln Thr Ser Trp Asn Glu
            1140                1145                1150

Ala Cys Ser Cys Asn Gly Gly Arg Gly Glu Gly Cys Pro Lys Asn Thr
        1155                1160                1165

Val Asp Gly Asp Asp Ser Gly Glu Gly Leu Tyr Val Pro Phe Cys Phe
    1170                1175                1180

Cys Lys Lys Gly Lys Pro Gly Lys Thr Glu Arg Leu Arg Phe Ile Ser
1185                1190                1195                1200
```

-continued

```
Gly Phe Leu Gln Ile Lys Met Ala Ile Ile Thr Glu
            1205                1210
```

```
<210> SEQ ID NO 4
<211> LENGTH: 1212
<212> TYPE: PRT
<213> ORGANISM: Rattus rattus
<220> FEATURE:
<221> NAME/KEY: SITE
<222> LOCATION: (43)
<223> OTHER INFORMATION: Xaa is any amino acid.
<220> FEATURE:
<221> NAME/KEY: SITE
<222> LOCATION: (1103)
<223> OTHER INFORMATION: Xaa is any amino acid.

<400> SEQUENCE: 4
```

```
Gly Ala Ser Ala Gly Gly Gly His Val Ala Ala Ala Ala Ala Ala Ala
 1               5                  10                  15

Ala Ala Ala Ala Ala Ala Ala Ala Ser Val Arg Gly Ala Gly
             20                  25                  30

Arg Pro Pro Ser Phe Leu Arg Arg Gln Pro Xaa Phe Pro Pro Leu Gly
             35                  40                  45

Ser Pro Gly Ser Thr Leu Pro Ala Gly Ser Cys Ser Leu Leu Phe Leu
     50                  55                  60

Val Ser Ser His Arg Thr Arg Arg Gly Ala Arg Ser Ala Ala Thr Met
 65                  70                  75                  80

Gly Lys Gly Val Gly Arg Asp Lys Tyr Glu Pro Ala Ala Val Ser Glu
                 85                  90                  95

His Gly Asp Lys Lys Ser Lys Lys Ala Lys Lys Glu Arg Asp Met Asp
            100                 105                 110

Glu Leu Lys Lys Glu Val Ser Met Asp Asp His Lys Leu Ser Leu Asp
            115                 120                 125

Glu Leu His Arg Lys Tyr Gly Thr Asp Leu Ser Arg Gly Leu Thr Pro
        130                 135                 140

Ala Arg Ala Ala Glu Ile Leu Ala Arg Asp Gly Pro Asn Ala Leu Thr
145                 150                 155                 160

Pro Pro Pro Thr Thr Pro Glu Trp Val Lys Phe Cys Arg Gln Leu Phe
                165                 170                 175

Gly Gly Phe Ser Met Leu Leu Trp Ile Gly Ala Ile Leu Cys Phe Leu
            180                 185                 190

Ala Tyr Gly Ile Arg Ser Ala Thr Glu Glu Pro Pro Asn Asp Asp
        195                 200                 205

Leu Tyr Leu Gly Val Val Leu Ser Ala Val Ile Ile Thr Gly Cys
    210                 215                 220

Phe Ser Tyr Tyr Gln Glu Ala Lys Ser Ser Lys Ile Met Glu Ser Phe
225                 230                 235                 240

Lys Asn Met Val Pro Gln Gln Ala Leu Val Ile Arg Asn Gly Glu Lys
                245                 250                 255

Met Ser Ile Asn Ala Glu Asp Val Val Gly Asp Leu Val Glu Val
            260                 265                 270

Lys Gly Gly Asp Arg Ile Pro Ala Asp Leu Arg Ile Ile Ser Ala Asn
        275                 280                 285

Gly Cys Lys Val Asp Asn Ser Ser Leu Thr Gly Glu Ser Glu Pro Gln
    290                 295                 300

Thr Arg Ser Pro Asp Phe Thr Asn Glu Asn Pro Leu Glu Thr Arg Asn
305                 310                 315                 320
```

-continued

```
Ile Ala Phe Phe Ser Thr Asn Cys Val Glu Gly Thr Ala Arg Gly Ile
                325                 330                 335

Val Val Tyr Thr Gly Asp Arg Thr Val Met Gly Arg Ile Ala Thr Leu
            340                 345                 350

Ala Ser Gly Leu Glu Gly Gly Gln Thr Pro Ile Ala Glu Gly Ile Glu
        355                 360                 365

His Phe Ile His Leu Ile Thr Gly Val Ala Val Phe Leu Gly Val Ser
    370                 375                 380

Phe Phe Ile Leu Ser Leu Ile Leu Glu Tyr Thr Trp Leu Glu Ala Val
385                 390                 395                 400

Ile Phe Leu Ile Gly Ile Ile Val Ala Asn Val Pro Glu Gly Leu Leu
            405                 410                 415

Ala Thr Val Thr Val Cys Leu Thr Leu Thr Ala Lys Arg Met Ala Arg
            420                 425                 430

Lys Asn Cys Leu Val Lys Asn Leu Glu Ala Val Glu Thr Leu Gly Ser
        435                 440                 445

Thr Ser Thr Ile Cys Ser Asp Lys Thr Gly Thr Leu Thr Gln Asn Arg
    450                 455                 460

Met Thr Val Ala His Met Trp Phe Asp Asn Gln Ile His Glu Ala Asp
465                 470                 475                 480

Thr Thr Glu Asn Gln Ser Gly Val Ser Phe Asp Lys Thr Ser Ala Thr
            485                 490                 495

Trp Phe Ala Leu Ser Arg Ile Ala Gly Leu Cys Asn Arg Ala Val Phe
            500                 505                 510

Gln Ala Asn Gln Glu Asn Leu Pro Ile Leu Lys Arg Ala Val Ala Gly
        515                 520                 525

Asp Ala Ser Glu Ser Ala Leu Leu Lys Cys Ile Glu Val Cys Cys Gly
    530                 535                 540

Ser Val Met Glu Met Arg Glu Lys Tyr Thr Lys Ile Val Glu Ile Pro
545                 550                 555                 560

Phe Asn Ser Thr Asn Lys Tyr Gln Leu Ser Ile His Lys Asn Pro Asn
            565                 570                 575

Ala Ser Glu Pro Lys His Leu Leu Val Met Lys Gly Ala Pro Glu Arg
            580                 585                 590

Ile Leu Asp Arg Cys Ser Ser Ile Leu Leu His Gly Lys Glu Gln Pro
        595                 600                 605

Leu Asp Glu Glu Leu Lys Asp Ala Phe Gln Asn Ala Tyr Leu Glu Leu
    610                 615                 620

Gly Gly Leu Gly Glu Arg Val Leu Gly Phe Cys His Leu Leu Leu Pro
625                 630                 635                 640

Asp Glu Gln Phe Pro Glu Gly Phe Gln Phe Asp Thr Asp Glu Val Asn
            645                 650                 655

Phe Pro Val Asp Asn Leu Cys Phe Val Gly Leu Ile Ser Met Ile Asp
            660                 665                 670

Pro Pro Arg Ala Ala Val Pro Asp Ala Val Gly Lys Cys Arg Ser Ala
        675                 680                 685

Gly Ile Lys Val Ile Met Val Thr Gly Asp His Pro Ile Thr Ala Lys
    690                 695                 700

Ala Ile Ala Lys Gly Val Gly Ile Ile Ser Glu Gly Asn Glu Thr Val
705                 710                 715                 720

Glu Asp Ile Ala Ala Arg Leu Asn Ile Pro Val Asn Gln Val Asn Pro
            725                 730                 735

Arg Asp Ala Lys Ala Cys Val Val His Gly Ser Asp Leu Lys Asp Met
```

-continued

```
                      740                745                750
Thr Ser Glu Glu Leu Asp Asp Ile Leu Arg Tyr His Thr Glu Ile Val
            755                760                765
Phe Ala Arg Thr Ser Pro Gln Gln Lys Leu Ile Ile Val Glu Gly Cys
    770                775                780
Gln Arg Gln Gly Ala Ile Val Ala Val Thr Gly Asp Gly Val Asn Asp
785                790                795                800
Ser Pro Ala Leu Lys Lys Ala Asp Ile Gly Val Ala Met Gly Ile Val
                805                810                815
Gly Ser Asp Val Ser Lys Gln Ala Ala Asp Met Ile Leu Leu Asp Asp
            820                825                830
Asn Phe Ala Ser Ile Val Thr Gly Val Glu Glu Gly Arg Leu Ile Phe
        835                840                845
Asp Asn Leu Lys Lys Ser Ile Ala Tyr Thr Leu Thr Ser Asn Ile Pro
850                855                860
Glu Ile Thr Pro Phe Leu Ile Phe Ile Ile Ala Asn Ile Pro Leu Pro
865                870                875                880
Leu Gly Thr Val Thr Ile Leu Cys Ile Asp Leu Gly Thr Asp Met Val
                885                890                895
Pro Ala Ile Ser Leu Ala Tyr Glu Gln Ala Glu Ser Asp Ile Met Lys
            900                905                910
Arg Gln Pro Arg Asn Pro Lys Thr Asp Lys Leu Val Asn Glu Arg Leu
        915                920                925
Ile Ser Met Ala Tyr Gly Gln Ile Gly Met Ile Gln Ala Leu Gly Gly
    930                935                940
Phe Phe Thr Tyr Phe Val Ile Leu Ala Glu Asn Gly Phe Leu Pro Phe
945                950                955                960
His Leu Leu Gly Ile Arg Glu Thr Trp Asp Asp Arg Trp Ile Asn Asp
                965                970                975
Val Glu Asp Ser Tyr Gly Gln Gln Trp Thr Tyr Glu Gln Arg Lys Ile
            980                985                990
Val Glu Phe Thr Cys His Thr Ala Phe Phe Val Ser Ile Val Val Val
        995                1000               1005
Gln Trp Ala Asp Leu Val Ile Cys Lys Thr Arg Arg Asn Ser Val Phe
    1010               1015               1020
Gln Gln Gly Met Lys Asn Lys Ile Leu Ile Phe Gly Leu Phe Glu Glu
1025               1030               1035               1040
Thr Ala Leu Ala Ala Phe Leu Ser Tyr Cys Pro Gly Met Gly Ala Ala
                1045               1050               1055
Leu Arg Met Tyr Pro Leu Lys Pro Thr Trp Trp Phe Cys Ala Phe Pro
            1060               1065               1070
Tyr Ser Leu Leu Ile Phe Val Tyr Asp Glu Val Arg Lys Leu Ile Ile
        1075               1080               1085
Arg Arg Arg Pro Gly Gly Trp Val Glu Lys Glu Thr Tyr Tyr Xaa Pro
    1090               1095               1100
Thr Ala Leu His Ala Val Glu His Cys Ala Thr His Cys Thr Tyr Pro
1105               1110               1115               1120
Tyr Pro Pro Phe Val Tyr Phe Lys Ser Trp Ser Ser Glu Leu Tyr Pro
                1125               1130               1135
Gly Arg Lys Ala Pro Lys His Val Gly Ile Gln Thr Ser Trp Asn Glu
            1140               1145               1150
Ala Cys Ser Cys Asn Gly Gly Arg Gly Glu Gly Cys Pro Lys Asn Thr
        1155               1160               1165
```

-continued

Val Asp Gly Asp Asp Ser Gly Glu Gly Leu Tyr Val Pro Phe Cys Phe
    1170             1175             1180

Cys Lys Lys Gly Lys Pro Gly Lys Thr Glu Arg Leu Arg Phe Ile Ser
1185             1190             1195             1200

Gly Phe Leu Gln Ile Lys Met Ala Ile Ile Thr Glu
            1205             1210

<210> SEQ ID NO 5
<211> LENGTH: 3636
<212> TYPE: DNA
<213> ORGANISM: Rattus rattus

<400> SEQUENCE: 5

| | | | | | |
|---|---|---|---|---|---|
| ggagcctcgg | cgggaggagg | cggacacgtg | gcagcggcgg | cggcagcggc | agcagcagcg | 60 |
| gcggcagcag | cggcggcctc | ggtccggggc | gccggccgtc | ctccctcttt | cctccggcgg | 120 |
| cagccctagt | tccgcctct | cggctccccc | ggctccactc | tcccagccgg | gagctgctct | 180 |
| ctcctctttc | tagtctccag | ccacaggacc | cggcgcgggg | cccgcagcgc | cgccaccatg | 240 |
| gggaaggggg | ttggacgaga | caagtatgag | cccgcagctg | tatcagaaca | tggggacaag | 300 |
| aagagcaaga | aggcgaagaa | ggaaagggac | atggacgaac | tcaagaagga | agtgtctatg | 360 |
| gacgaccata | aactcagcct | ggatgaactc | catcgtaaat | acggaacaga | tttgagccga | 420 |
| ggcctaacac | ccgcaagggc | cgctgagatc | ctggctcggg | atggccccaa | cgccctcacg | 480 |
| ccccctccca | ctactcccga | gtgggtcaaa | ttctgtcggc | agctgttcgg | tggcttctcc | 540 |
| atgttactgt | ggattggagc | cattctttgt | ttcttggctt | atggcatccg | aagtgctaca | 600 |
| gaagaggaac | caccaaatga | tgatctgtac | ctcggggtcg | tgctgtctgc | tgtcgtcatc | 660 |
| ataactggct | gtttctccta | ttatcaagaa | gcaaaaagct | ccaagatcat | ggaatccttc | 720 |
| aagaacatgg | tccctcagca | agccctcgtg | attcgaaatg | gagagaagat | gagcatcaac | 780 |
| gcagaggatg | tcgtcgttgg | tgatctggtg | gaggtgaagg | gcggagaccg | aatccctgct | 840 |
| gatctcagaa | tcatatctgc | aaatggctgc | aaggtggata | actcctcact | cactggtgaa | 900 |
| tcagaacccc | agactcggtc | cccggatttc | acaaacgaga | ccccttgga | dacaaggaac | 960 |
| attgccttct | tctcaaccaa | ctgtgttgaa | ggaactgcac | gtggcatcgt | tgtgtacact | 1020 |
| ggggatcgca | ccgtgatggg | caggatcgcc | acccttgctt | ctgggctgga | aggcggccag | 1080 |
| accccccattg | ctgaagaaat | cgagcacttc | atccacctca | tcacgggtgt | ggccgtgttc | 1140 |
| ctggggtgt | ctttcttcat | tctctctctg | atccttgagt | acacctggct | cgaggctgtc | 1200 |
| atcttcctca | ttggtatcat | cgtagccaac | gtgccggaag | gtttgctggc | caccgtcacg | 1260 |
| gtatgtctga | cgctcactgc | caagcgcatg | gcgaggaaga | actgcctggt | gaagaacctg | 1320 |
| gaagctgtgg | agaccttggg | gtccacatcc | accatctgct | ccgacaagac | tggaactctg | 1380 |
| actcagaacc | ggatgacagt | ggctcacatg | tggtttgaca | atcaaatcca | tgaagctgac | 1440 |
| accacagaga | atcagagtgg | ggtctccttt | gacaagacgt | cagccacctg | gttcgctctg | 1500 |
| tccagaattg | ctggtctctg | taacagggca | gtgtttcagg | ctaaccaaga | aaacctgcct | 1560 |
| atccttaagc | gtgcagtagc | gggagatgct | tccgagtcgg | cgctcttaaa | gtgcatcgag | 1620 |
| gtctgctgtg | gctccgtgat | ggagatgagg | gagaagtaca | ccaagatagt | ggagattcct | 1680 |
| ttcaactcca | ccaacaagta | ccagctctcc | attcacaaga | acccaaacgc | atcggagcct | 1740 |
| aagcacctgc | tagtgatgaa | gggcgcccca | gaaaggatcc | tggaccgatg | cagttctatc | 1800 |
| ctcctccacg | gcaaggagca | gccctggac | gaagagctga | aggacgcctt | tcagaatgcc | 1860 |

```
tacctagagc tgggggcct tggagagcgt gtgctaggtt tctgccacct ccttctgcct    1920
gacgaacagt ttcccgaagg cttccagttt gacactgatg aagtcaattt ccccgtggat    1980
aacctctgct tcgtgggtct tatctccatg attgaccctc ctcgagctgc tgtccccgat    2040
gctgtgggca aatgccgcag cgctgggatt aaggtcatca tggtcacagg agaccatcca    2100
atcacagcca aagccattgc taaggggtg ggcattatct cagaaggtaa cgagaccgtg    2160
gaagacattg ctgcccgcct caacattcca gtgaaccagg tgaacccag agatgccaag    2220 gcctgtgtag tacatggcag tgacttgaag gacatgacct ctgaggagct ggatgacatt    2280
ttgcggtacc acacggagat tgtctttgct aggacctctc ctcaacagaa gctcatcatt    2340
gtggagggct gccagcggca gggtgccatc gtggctgtca caggggatgg tgtcaatgac    2400
tctccagctt tgaaaaaggc agatattggg gttgccatgg ggattgttgg ctcggatgtg    2460
tccaagcaag ctgctgacat gattcttctg gatgacaact ttgcctccat cgtgactgga    2520
gtagaagaag tcgtctgat atttgataac ttgaagaaat ccattgctta caccctaaca    2580
agtaacattc cggaaatcac ccccttcttg atatttatta ttgcaaacat tccatgtccc    2640
ctgggcaccg tgaccatcct ctgcattgac ttgggcactg acatggttcc cgccatctct    2700
ctggcctatg aacaggctga aagtgacatc atgaagaggc agcccagaaa tcccaaaacg    2760
gacaaacttg tgaacgagcg tctgatcagc atggcctatg acagatcgg tatgatccag    2820 gccctgggag gcttcttcac ttattttgtg attctggctg agaacggttt cctgcccttt    2880
cacctgttgg gcatccgaga gacctgggat gaccgctgga tcaatgatgt ggaggacagc    2940
tacgggcagc agtggaccta cgagcagagg aagattgtgg agttcacctg ccacacggcc    3000
ttctttgtca gtatcgtggt agtgcagtgg gctgacttgg tcatctgcaa gaccagaagg    3060
aattctgtct tccagcaggg aatgaagaac aagatcttaa tatttggcct cttttgaagag    3120 acagctcttg ctgctttcct gtcctactgc cctgggatgg gtgcagccct taggatgtat    3180
cccctcaaac ctacttggtg gttctgtgcc ttccccctact cccttctcat cttcgtgtat    3240
gacgaggtgc ggaagctcat catcaggcga cgccctggcg gctgggtgga aaggaaaacc    3300
tactactagc ccactgccct gcacgccgtg gaacattgtg ccacacactg cacctacccc    3360 tacccccct ttgtgtactt caagtcttgg agctcggaac tctaccctgg taggaaagca    3420
ccaaagcatg tggggatcca gacgtcctgg aatgaagcat gtagctgtaa tgggggcgg    3480 ggggagggct gcccgaaaaa caccgtggac ggggacgaca gcggggaagg tttatatgtg    3540
cctttttgtt tttgtaaaaa aggaaaaacct ggaaagactg aaagattacg ttttatatct    3600
ggatttttac aaataaagat ggctattata acggaa                              3636
```

<210> SEQ ID NO 6  
<211> LENGTH: 3636  
<212> TYPE: DNA  
<213> ORGANISM: Rattus rattus

<400> SEQUENCE: 6

```
ggagcctcgg cgggaggagg cggacacgtg gcagcggcgg cggcagcggc agcagcagcg     60
gcggcagcag cggcggcctc ggtccggggc gccggccgtc ctccctcttt cctccggcgg    120
cagccctagt tcccgcctct cggctccccc ggctccactc tcccagccgg gagctgctct    180
ctcctctttc tagtctccag ccacaggacc cggcgcgggg cccgcagcgc cgccaccatg    240
gggaaggggg ttggacgaga caagtatgag cccgcagctg tatcagaaca tggggacaag    300
```

-continued

| | |
|---|---|
| aagagcaaga aggcgaagaa ggaaagggac atggacgaac tcaagaagga agtgtctatg | 360 |
| gacgaccata aactcagcct ggatgaactc catcgtaaat acggaacaga tttgagccga | 420 |
| ggcctaacac ccgcaagggc cgctgagatc ctggctcggg atgccccaa cgccctcacg | 480 |
| cccctccca ctactcccga gtgggtcaaa ttctgtcggc agctgttcgg tggcttctcc | 540 |
| atgttactgt ggattggagc cattctttgt ttcttggctt atggcatccg aagtgctaca | 600 |
| gaagaggaac caccaaatga tgatctgtac ctcggggtcg tgctgtctgc tgtcgtcatc | 660 |
| ataactggct gtttctccta ttatcaagaa gcaaaaagct ccaagatcat ggaatccttc | 720 |
| aagaacatgg tccctcagca agccctcgtg attcgaaatg agagaagat gagcatcaac | 780 |
| gcagaggatg tcgtcgttgg tgatctggtg gaggtgaagg gcggagaccg aatccctgct | 840 |
| gatctcagaa tcatatctgc aaatggctgc aaggtggata actcctcact cactggtgaa | 900 |
| tcagaaccc agactcggtc cccggatttc acaaacgaga ccccttgga gacaaggaac | 960 |
| attgccttct tctcaaccaa ctgtgttgaa ggaactgcac gtggcatcgt tgtgtacact | 1020 |
| gggatcgca ccgtgatggg caggatcgcc acccttgctt ctgggctgga aggcggccag | 1080 |
| accccccattg ctgaagaaat cgagcacttc atccacctca tcacgggtgt ggccgtgttc | 1140 |
| ctggggtgt ctttcttcat tctctctctg atccttgagt acacctggct cgaggctgtc | 1200 |
| atcttcctca ttggtatcat cgtagccaac gtgccggaag gtttgctggc caccgtcacg | 1260 |
| gtatgtctga cgctcactgc caagcgcatg gcgaggaaga actgcctggt gaagaacctg | 1320 |
| gaagctgtgg agaccttggg gtccacatcc accatctgct ccgacaagac tggaactctg | 1380 |
| actcagaacc ggatgacagt ggctcacatg tggtttgaca tcaaatcca tgaagctgac | 1440 |
| accacagaga atcagagtgg ggtctccttt gacaagacgt cagccacctg gttcgctctg | 1500 |
| tccagaattg ctggtctctg taacagggca gtgtttcagg ctaaccaaga aaacctgcct | 1560 |
| atccttaagc gtgcagtagc gggagatgct tccgagtcgg cgctcttaaa gtgcatcgag | 1620 |
| gtctgctgtg gctccgtgat ggagatgagg gagaagtaca ccaagatagt ggagattcct | 1680 |
| ttcaactcca ccaacaagta ccagctctcc attcacaaga cccaaacgc atcggagcct | 1740 |
| aagcacctgc tagtgatgaa gggcgcccca gaaaggatcc tggaccgatg cagttctatc | 1800 |
| ctcctccacg gcaaggagca gccctggac gaagagctga aggacgcctt tcagaatgcc | 1860 |
| tacctagagc tgggggggcct tggagagcgt gtgctaggtt tctgccacct ccttctgcct | 1920 |
| gacgaacagt ttcccgaagg cttccagttt gacactgatg aagtcaattt ccccgtggat | 1980 |
| aacctctgct tcgtgggtct tatctccatg attgaccctc ctcgagctgc tgtccccgat | 2040 |
| gctgtgggca aatgccgcag cgctgggatt aaggtcatca tggtcacagg agaccatcca | 2100 |
| atcacagcca aagccattgc taagggggtg gcattatct cagaaggtaa cgagaccgtg | 2160 |
| gaagacattg ctgcccgcct caacattcca gtgaaccagg tgaaccccag agatgccaag | 2220 |
| gcctgtgtag tacatggcag tgacttgaag gacatgacct ctgaggagct ggatgacatt | 2280 |
| ttgcggtacc acacggagat tgtctttgct aggacctctc ctcaacagaa gctcatcatt | 2340 |
| gtggagggct gccagcggca gggtgccatc gtggctgtca caggggatgg tgtcaatgac | 2400 |
| tctccagctt tgaaaaaggc agatattggg gttgccatgg ggattgttgg ctcggatgtg | 2460 |
| tccaagcaag ctgctgacat gattcttctg gatgacaact ttgcctccat cgtgactgga | 2520 |
| gtagaagaag gtcgtctgat atttgataac ttgaagaaat ccattgctta caccctaaca | 2580 |
| agtaacattc cggaaatcac ccccttcttg atatttatta ttgcaaacat tccactgccc | 2640 |
| tgtggcaccg tgaccatcct ctgcattgac ttgggcactg acatggttcc cgccatctct | 2700 |

```
ctggcctatg aacaggctga aagtgacatc atgaagaggc agcccagaaa tcccaaaacg   2760
gacaaacttg tgaacgagcg tctgatcagc atggcctatg acagatcgg tatgatccag    2820 gccctgggag gcttcttcac ttattttgtg attctggctg agaacggttt cctgcccttt    2880
cacctgttgg gcatccgaga gacctgggat gaccgctgga tcaatgatgt ggaggacagc    2940
tacgggcagc agtggaccta cgagcagagg aagattgtgg agttcacctg ccacacggcc    3000
ttctttgtca gtatcgtggt agtgcagtgg gctgacttgg tcatctgcaa gaccagaagg    3060
aattctgtct tccagcaggg aatgaagaac aagatcttaa tatttggcct cttgaagag    3120 acagctcttg ctgctttcct gtcctactgc cctgggatgg gtgcagccct taggatgtat    3180
cccctcaaac ctacttggtg gttctgtgcc ttccccctact cccttctcat cttcgtgtat    3240
gacgaggtgc ggaagctcat catcaggcga cgcctggcg gctgggtgga aaggaaacc    3300 tactactagc ccactgccct gcacgccgtg aacattgtg ccacacactg cacctacccc    3360 tacccccct tgtgtactt caagtcttgg agctcggaac tctaccctgg taggaaagca    3420
ccaaagcatg tggggatcca gacgtcctgg aatgaagcat gtagctgtaa tggggggcgg    3480
ggggagggct gcccgaaaaa caccgtggac ggggacgaca gcgggggaagg tttatatgtg    3540 ccttttgtt tttgtaaaaa aggaaaaacct ggaaagactg aaagattacg ttttatatct    3600 ggattttac aaataaagat ggctattata acggaa                              3636

<210> SEQ ID NO 7
<211> LENGTH: 3636
<212> TYPE: DNA
<213> ORGANISM: Rattus rattus

<400> SEQUENCE: 7
ggagcctcgg cgggaggagg cggacacgtg gcagcggcgg cggcagcggc agcagcagcg     60
gcggcagcag cggcggcctc ggtccggggc gccggccgtc ctccctcttt cctccggcgg    120
cagccctagt tcccgcctct cggctccccc ggctccactc tcccagccgg gagctgctct    180
ctcctctttc tagtctccag ccacaggacc cggcgcgggg cccgcagcgc cgccaccatg    240
gggaaggggg ttggacgaga caagtatgag cccgcagctg tatcagaaca tggggacaag    300
aagagcaaga aggcgaagaa ggaaagggac atggacgaac tcaagaagga agtgtctatg    360
gacgaccata aactcagcct ggatgaactc atcgtaaat acggaacaga tttgagccga    420
ggcctaacac ccgcaagggc cgctgagatc ctggctcggg atggcccaa cgccctcacg    480 ccccctccca ctactcccga gtgggtcaaa ttctgtcggc agctgttcgg tggcttctcc    540
atgttactgt ggattggagc cattctttgt ttcttggctt atggcatccg aagtgctaca    600
gaagaggaac caccaaatga tgatctgtac ctcggggtcg tgctgtctgc tgtcgtcatc    660
ataactggct gtttctccta ttatcaagaa gcaaaaagct ccaagatcat ggaatccttc    720
aagaacatgg tccctcagca agccctcgtg attcgaaatg gagagaagat gagcatcaac    780
gcagaggatg tcgtcgttgg tgatctggtg gaggtgaagg gcggagaccg aatccctgct    840
gatctcagaa tcatatctgc aaatggctgc aaggtggata actcctcact cactggtgaa    900
tcagaacccc agactcggtc cccggatttc acaaacgaga ccccttgga caaggaac      960 attgccttct tctcaaccaa ctgtgttgaa ggaactgcac gtggcatcgt tgtgtacact   1020
ggggatcgca ccgtgatggg caggatcgcc acccttgctt ctgggctgga aggcggccag   1080 accccccattg ctgaagaaat cgagcacttc atccacctca tcacgggtgt ggccgtgttc   1140
```

-continued

```
ctggggtgt ctttcttcat tctctctctg atccttgagt acacctggct cgaggctgtc    1200
atcttcctca ttggtatcat cgtagccaac gtgccggaag gtttgctggc caccgtcacg    1260
gtatgtctga cgctcactgc caagcgcatg gcgaggaaga actgcctggt gaagaacctg    1320
gaagctgtgg agaccttggg gtccacatcc accatctgct ccgacaagac tggaactctg    1380
actcagaacc ggatgacagt ggctcacatg tggtttgaca atcaaatcca tgaagctgac    1440
accacagaga atcagagtgg ggtctccttt gacaagacgt cagccacctg gttcgctctg    1500
tccagaattg ctggtctctg taacagggca gtgtttcagg ctaaccaaga aaacctgcct    1560
atccttaagc gtgcagtagc gggagatgct tccgagtcgg cgctcttaaa gtgcatcgag    1620
gtctgctgtg gctccgtgat ggagatgagg gagaagtaca ccaagatagt ggagattcct    1680
ttcaactcca ccaacaagta ccagctctcc attcacaaga acccaaacgc atcggagcct    1740
aagcacctgc tagtgatgaa gggcgcccca gaaaggatcc tggaccgatg cagttctatc    1800
ctcctccacg gcaaggagca gcccctggac gaagagctga aggacgcctt tcagaatgcc    1860
tacctagagc tggggggcct tggagagcgt gtgctaggtt tctgccacct ccttctgcct    1920
gacgaacagt ttcccgaagg cttccagttt gacactgatg aagtcaattt ccccgtggat    1980
aacctctgct tcgtgggtct tatctccatg attgaccctc ctcgagctgc tgtccccgat    2040
gctgtgggca aatgccgcag cgctgggatt aaggtcatca tggtcacagg agaccatcca    2100
atcacagcca aagccattgc taaggggtgt ggcattatct cagaagtaa cgagaccgtg    2160 gaagacattg ctgcccgcct caacattcca gtgaaccagg tgaaccccag agatgccaag    2220
gcctgtgtag tacatggcag tgacttgaag gacatgacct ctgaggagct ggatgacatt    2280
ttgcggtacc acacggagat tgtctttgct aggacctctc ctcaacagaa gctcatcatt    2340
gtggagggct gccagcggca gggtgccatc gtggctgtca caggggatgg tgtcaatgac    2400
tctccagctt tgaaaaaggc agatattggg gttgccatgg ggattgttgg ctcggatgtg    2460
tccaagcaag ctgctgacat gattcttctg gatgacaact ttgcctccat cgtgactgga    2520
gtagaagaag gtcgtctgat atttgataac ttgaagaaat ccattgctta caccctaaca    2580
agtaacattc cggaaatcac ccccttcttg atatttatta ttgcaaacat tccatgtccc    2640
tgtggcaccg tgaccatcct ctgcattgac ttgggcactg acatggttcc cgccatctct    2700
ctggcctatg aacaggctga aagtgacatc atgaagaggc agcccagaaa tcccaaaacg    2760
gacaaacttg tgaacgagcg tctgatcagc atggcctatg acagatcgg tatgatccag    2820 gccctgggag gcttcttcac ttattttgtg attctggctg agaacggttt cctgcccttt    2880
cacctgttgg gcatccgaga gacctgggat gaccgctgga tcaatgatgt ggaggacagc    2940
tacgggcagc agtggaccta cgagcagagg aagattgtgg agttcacctg ccacacggcc    3000
ttctttgtca gtatcgtggt agtgcagtgg gctgacttgg tcatctgcaa gaccagaagg    3060
aattctgtct tccagcaggg aatgaagaac aagatcttaa tatttggcct ctttgaagag    3120
acagctcttg ctgcttttcct gtcctactgc cctgggatgg tgcagccct taggatgtat    3180 cccctcaaac ctacttggtg gttctgtgcc ttccctact cccttctcat cttcgtgtat    3240
gacgaggtgc ggaagctcat catcaggcga cgccctggcg gctgggtgga aaggaaacc    3300 tactactagc ccactgccct gcacgccgtg gaacattgtg ccacacactg cacctacccc    3360
taccccccct ttgtgtactt caagtcttgg agctcggaac tctaccctgg taggaaagca    3420
ccaaagcatg tgggatccaa gacgtcctgg aatgaagcat gtagctgtaa tgggggcgg    3480 gggagggct gcccgaaaaa caccgtggac ggggacgaca gcggggaagg tttatatgtg    3540
```

```
ccttttttgtt tttgtaaaaa aggaaaacct ggaaagactg aaagattacg ttttatatct    3600
ggatttttac aaataaagat ggctattata acggaa                              3636

<210> SEQ ID NO 8
<211> LENGTH: 3636
<212> TYPE: DNA
<213> ORGANISM: Rattus rattus

<400> SEQUENCE: 8
ggagcctcgg cgggaggagg cggacacgtg gcagcggcgg cggcagcggc agcagcagcg      60
gcggcagcag cggcggcctc ggtccggggc gccggccgtc ctccctcttt cctccggcgg     120
cagccctagt tcccgcctct cggctccccc ggctccactc tcccagccgg gagctgctct     180
ctcctctttc tagtctccag ccacaggacc cggcgcgggg cccgcagcgc cgccaccatg     240
gggaaggggg ttggacgaga caagtatgag cccgcagctg tatcagaaca tggggacaag     300
aagagcaaga aggcgaagaa ggaaagggac atggacgaac tcaagaagga agtgtctatg     360
gacgaccata aactcagcct ggatgaactc catcgtaaat acggaacaga tttgagccga     420
ggcctaacac ccgcaagggc cgctgagatc ctggctcggg atggccccaa cgccctcacg     480 cccccctccca ctactcccga gtgggtcaaa ttctgtcggc agctgttcgg tggcttctcc     540
atgttactgt ggattggagc cattctttgt ttcttggctt atggcatccg aagtgctaca     600
gaagaggaac caccaaatga tgatctgtac ctcggggtcg tgctgtctgc tgtcgtcatc     660
ataactggct gtttctccta ttatcaagaa gcaaaaagct ccaagatcat ggaatccttc     720
aagaacatgg tccctcagca agccctcgtg attcgaaatg agagaagat gagcatcaac     780 gcagaggatg tcgtcgttgg tgatctggtg gaggtgaagg gcggagaccg aatccctgct     840
gatctcagaa tcatatctgc aaatggctgc aaggtggata actcctcact cactggtgaa     900
tcagaacccc agactcggtc cccggatttc acaaacgaga acccttgga gacaaggaac     960 attgccttct tctcaaccaa ctgtgttgaa ggaactgcac gtggcatcgt tgtgtacact    1020
ggggatcgca ccgtgatggg caggatcgcc acccttgctt ctgggctgga aggcggccag    1080 accccccattg ctgaagaaat cgagcacttc atccacctca tcacgggtgt ggccgtgttc    1140 ctggggtgt ctttcttcat tctctctctg atccttgagt acacctggct cgaggctgtc    1200
atcttcctca ttggtatcat cgtagccaac gtgccggaag gtttgctggc caccgtcacg    1260
gtatgtctga cgctcactgc caagcgcatg gcgaggaaga actgcctggt gaagaacctg    1320
gaagctgtgg agaccttggg gtccacatcc accatctgct ccgacaagac tggaactctg    1380
actcagaacc ggatgacagt ggctcacatg tggtttgaca atcaaatcca tgaagctgac    1440
accacagaga atcagagtgg ggtctccttt gacaagacgt cagccacctg gttcgctctg    1500
tccagaattg ctggtctctg taacagggca gtgtttcagg ctaaccaaga aaacctgcct    1560
atccttaagc gtgcagtagc gggagatgct tccgagtcgg cgctcttaaa gtgcatcgag    1620
gtctgctgtg gctccgtgat ggagatgagg gagaagtaca ccaagatagt ggagattcct    1680
ttcaactcca ccaacaagta ccagctctcc attcacaaga cccaaacgc atcggagcct    1740 aagcacctgc tagtgatgaa gggcgcccca gaaaggatcc tggaccgatg cagttctatc    1800
ctcctccacg gcaaggagca gcccctggac gaagagctga aggacgcctt tcagaatgcc    1860
tacctagagc tgggggggcct tggagagcgt gtgctaggtt tctgccacct ccttctgcct    1920
gacgaacagt ttcccgaagg cttccagttt gacactgatg aagtcaattt ccccgtggat    1980
```

-continued

```
aacctctgct tcgtgggtct tatctccatg attgaccctc ctcgagctgc tgtccccgat      2040
gctgtgggca atgccgcag cgctgggatt aaggtcatca tggtcacagg agaccatcca      2100
atcacagcca aagccattgc taaggggtg ggcattatct cagaaggtaa cgagaccgtg      2160
gaagacattg ctgcccgcct caacattcca gtgaaccagg tgaaccccag agatgccaag      2220
gcctgtgtag tacatggcag tgacttgaag acatgacct ctgaggagct ggatgacatt       2280
ttgcggtacc acacggagat tgtctttgct aggacctctc ctcaacagaa gctcatcatt     2340
gtggagggct gccagcggca gggtgccatc gtggctgtca caggggatgg tgtcaatgac     2400
tctccagctt tgaaaaaggc agatattggg gttgccatgg ggattgttgg ctcggatgtg    2460
tccaagcaag ctgctgacat gattcttctg gatgacaact ttgcctccat cgtgactgga    2520
gtagaagaag gtcgtctgat atttgataac ttgaagaaat ccattgctta caccctaaca   2580
agtaacattc cggaaatcac ccccttcttg atatttatta ttgcaaacat tccactgccc    2640
ctgggcaccg tgaccatcct ctgcattgac ttgggcactg acatggttcc cgccatctct   2700
ctggcctatg aacaggctga aagtgacatc atgaagaggc agcccagaaa tcccaaaacg   2760
gacaaacttg tgaacgagcg tctgatcagc atggcctatg gacagatcgg tatgatccag  2820
gccctgggag gcttcttcac ttattttgtg attctggctg agaacggttt cctgcccttt    2880
cacctgttgg gcatccgaga gacctgggat gaccgctgga tcaatgatgt ggaggacagc   2940
tacgggcagc agtggaccta cgagcagagg aagattgtgg agttcacctg ccacacggcc   3000
ttctttgtca gtatcgtggt agtgcagtgg gctgacttgg tcatctgcaa gaccagaagg  3060
aattctgtct tccagcaggg aatgaagaac aagatcttaa tatttggcct ctttgaagag   3120
acagctcttg ctgctttcct gtcctactgc cctgggatgg gtgcagccct taggatgtat   3180
cccctcaaac ctacttggtg gttctgtgcc ttcccctact cccttctcat cttcgtgtat  3240
gacgaggtgc ggaagctcat catcaggcga cgccctggcg gctgggtgga gaaggaaacc    3300
tactactagc ccactgccct gcacgccgtg gaacattgtg ccacacactg cacctacccc   3360
taccccccct tgtgtactt caagtcttgg agctcggaac tctaccctgg taggaaagca  3420
ccaaagcatg tggggatcca gacgtcctgg aatgaagcat gtagctgtaa tggggggcgg   3480
ggggagggct gcccgaaaaa caccgtggac ggggacgaca gcggggaagg tttatatgtg   3540
cctttttgtt tttgtaaaaa aggaaaacct ggaaagactg aaagattacg ttttatatct  3600
ggatttttac aaataaagat ggctattata acggaa                              3636
```

<210> SEQ ID NO 9
<211> LENGTH: 20
<212> TYPE: PRT
<213> ORGANISM: synthetic construct
<220> FEATURE:
<221> NAME/KEY: SITE
<222> LOCATION: (9)
<223> OTHER INFORMATION: Xaa is Cys, Leu, Gly, Ala, Val, or Ile, and at
      least one Xaa at location 9, 11, 17, or 18 is Cys
<220> FEATURE:
<221> NAME/KEY: SITE
<222> LOCATION: (11)
<223> OTHER INFORMATION: Xaa is Cys, Leu, Gly, Ala, Val, or Ile, and at
      least one Xaa at location 9, 11, 17, or 18 is Cys
<220> FEATURE:
<221> NAME/KEY: SITE
<222> LOCATION: (17)..(18)
<223> OTHER INFORMATION: Xaa is Cys, Leu, Gly, Ala, Val, or Ile, and at
      least one Xaa at location 9, 11, 17, or 18 is Cys

<400> SEQUENCE: 9

```
Ile Phe Ile Ile Ala Asn Ile Pro Xaa Pro Xaa Gly Thr Val Thr Ile
  1               5                  10                  15

Xaa Xaa Ile Asp
         20
```

<210> SEQ ID NO 10
<211> LENGTH: 20
<212> TYPE: PRT
<213> ORGANISM: synthetic construct

<400> SEQUENCE: 10

```
Ile Phe Ile Ile Ala Asn Ile Pro Cys Pro Leu Gly Thr Val Thr Ile
  1               5                  10                  15

Leu Cys Ile Asp
         20
```

<210> SEQ ID NO 11
<211> LENGTH: 20
<212> TYPE: PRT
<213> ORGANISM: synthetic construct

<400> SEQUENCE: 11

```
Ile Phe Ile Ile Ala Asn Ile Pro Leu Pro Cys Gly Thr Val Thr Ile
  1               5                  10                  15

Leu Cys Ile Asp
         20
```

<210> SEQ ID NO 12
<211> LENGTH: 20
<212> TYPE: PRT
<213> ORGANISM: synthetic construct

<400> SEQUENCE: 12

```
Ile Phe Ile Ile Ala Asn Ile Pro Cys Pro Cys Gly Thr Val Thr Ile
  1               5                  10                  15

Leu Cys Ile Asp
         20
```

<210> SEQ ID NO 13
<211> LENGTH: 24
<212> TYPE: DNA
<213> ORGANISM: synthetic construct

<400> SEQUENCE: 13
atgattgacc ctcctcgagc tgct                                    24

<210> SEQ ID NO 14
<211> LENGTH: 24
<212> TYPE: DNA
<213> ORGANISM: synthetic construct

<400> SEQUENCE: 14
aataaatatc aagaaggggg tgat                                    24

<210> SEQ ID NO 15
<211> LENGTH: 22
<212> TYPE: DNA
<213> ORGANISM: synthetic construct

<400> SEQUENCE: 15
ggcctggatc ataccgatct gt                                      22

```
<210> SEQ ID NO 16
<211> LENGTH: 25
<212> TYPE: DNA
<213> ORGANISM: synthetic construct

<400> SEQUENCE: 16
attgcaaaca ttccatgtcc cctgg                                     25

<210> SEQ ID NO 17
<211> LENGTH: 27
<212> TYPE: DNA
<213> ORGANISM: synthetic construct

<400> SEQUENCE: 17
gtttgcaata ataaatatca agaaggg                                   27

<210> SEQ ID NO 18
<211> LENGTH: 25
<212> TYPE: DNA
<213> ORGANISM: synthetic construct

<400> SEQUENCE: 18
attccactgc cctgtggcac cgtga                                     25
```

SELECTION MARKER

This application claims benefit of Provisional No. 60/048,601 filed Jun. 4, 1997.

The present invention relates to a new method for selecting cells which involves a mutated naturally occuring life-essential enzyme, namely a (Na,K)-ATPase (EC 3.6.1.3). A mutated naturally occuring (Na,K)-ATPase or a subunit thereof, as well as their medical use is claimed. Also transgenic animals are claimed.

When transfecting genes to cells or individuals, a selection is often required and multiplication of the cells which have received the new gene is desirable. This can be done in many ways. Today a usual procedure is to simultaneously use genes which are resistant to antibiotics or cytostatics which makes the cells with the new gene resistant to these substances. It is then possible to make a selection between host cells which have received the intibiotic resistance gene and those host cells who have not by using the corresponding antibiotic. This is a well-known procedure for a person skilled in the art. (See e.g. Gene transfer and expression protocols. (Murray E. J, ed) Humana Press, New Jersey)

This procedure however have some disadvantages. It is expensive and may disturb the host cell due to the fact that an artificial gene has to be put in together with a certain selected gene. The cells must be selected using antibiotics or cytostatics. These antibiotic and cytostatic compounds might also interfere with other cellular mechanisms. It is not suitable to insert genes confering antibiotic or cytostatic resistance to human cells in the case of gene therapy. A current problem with gene therapy today is that the efficiency is low; possibly due to the low level of gene transfected cells.

Accordingly, there is a need for a new method for selection of cells which lack these disadvantages.

SUMMARY OF THE INVENTION

It has now been found, that by using a protein comprising the amino acid sequence: IFIIANIPXPXGTVTIXXID (SEQ ID NO:9) where X is chosen from the group of amino acids: cysteine, leucine, glycine, alanine, valine, isoleucine, where at least one X is cysteine, as a marker for screening cells, most of the drawbacks listed above can be overcome. Preferably the protein comprises at least one of the following three amino acid sequences: IFIIANIPCPLGTVTILCID (SEQ ID NO:10), IFIIANIPLPCGTVTILCID (SEQ ID NO:11) or IFIIANIPCPCGTVTILCID (SEQ ID NO:12).

Accordingly a new selection system fulfilling the above mentioned needs has now been discovered. The system is based upon using a protein already existing in the cell protein as selection gene namely (Na,K)-ATPase, EC 3.6.1, 3. This enzyme is essential for the cell and the gene is expressed in all mammalian cells. The (Na,K)-ATPase (a.k.a. Na+,K+-ATPase or NKA) is essential for the cell and it transports the sodium and potassium ions over the cell membrane. Without the function of this enzyme the cell will die In this system, such a gene has been mutated in a particular manner which causes a loss in sensitivity to the substance ouabain (a cardiotonic steroid or glycoside). This substance is able to kill all cells which have not received the mutated protein and surviving cells are only cells which have received the mutated gene product. Ouabain normally depresses the activity of (Na,K)-ATPase.

There are advantages with this new system. No heterologous gene has to be added to the cells. This minor mutation is more natural than adding an artificial gene or making some major mutations. Moreover, the selection substance ouabain is also relatively cheap and stable. Ouabain is neither an antibiotic substance nor a cytostatic compound. In gene therapy, it will not be necessery to screen using antibiotic or cytostatic compounds. The possibilty is also given to purify and multiply only interesting cells for gene therapy (e.g. heinatopoetic stemcells) with minimal intervention in the natural system of the cell. This new system gives an improved possibility of transporting new genes into cells from humans and animals. This can also improve the results in gene therapy and transplantation of e.g. hematopoetic stem cells, which have been subjected to gene therapy, to humans. Due to the fact that selection can be carried out with an enzyme, preferably NKA, which is already situated in the cell, an immunological answer on the transfected cells is minimized or eliminated when the cells are transplanted into a patient, e.g. when stem cell transplanting stem cells to a to human. The risk for an immunological reaction to occur must be regarded to be much higher when using a selection gene which is normally not expressed in the cell. There is also a new possibility to study effects of cardiac glycosides (e.g. digitalis) on cells or whole animals who are resistant to these drugs. This ouabain-resistant enzyme could also be very useful when studying the enzyme or its biological effects.

We will now go into further details of the invention.

DETAILED DESCRIPTION OF THE INVENTION

The protein encoded by the gene as well as variants, subfragments and multiples of the protein having essentially the same antigenic and/or binding characteristics also constitutes an object of the present invention. The new protein is referred to as 799/801NKA. Preferably the amino acid sequence of the 799/801NKA should be at least 70% homologous, more prefarbly at least 85% homologous, still more preferably at least 90% homologous and most preferably at least 95% homologous to anyone of the amino acid sequences disclosed in SEQ ID NOS 1, 2, 3. Preferably 799/801NKA has either a cysteine in position 799 or in position 801 or a cysteine in both positions. When we call the protein life-essential later in this document we mean that the cell can not survive without its function.

By "subfragments" is meant a part-fragment of the given protein in having essentially the same antigenic and /or binding characteristics. By "variants" is meant proteins or peptides in which the original amino acid sequence has been modified or changed by insertion, addition, substitution, inversion, or exclusion of one or more amino acids. By "multiples" is meant those proteins containing multiples of the whole original protein or those protein containing multiples of subfragments and/or variants thereof.

The present invention also relates to nucleic acid sequences encoding 799/801NKA As utilized within the context of the present invention, nucleic acid sequences which encode 799/801NKA are deemed to be substantially similar to those disclosed herein if; (a) the nucleic acid sequence is derived from the coding region of a native NKA gene (including, for example, variations of the sequences disclosed herein); (b) the nucleic acid sequence is capable of hybridization to nucleic acid sequences of the present invention under conditions of either moderate or high stringency (hybridization in 5×SSPE containing 0 1% SDS and 0.1 mg/ml ssDNA, at 50–65°/C. dependent on the probe length, or 10–20°/C. below the $T_m$ of the probe; washing in 1×SSPE, 0.1% SDS at 1 5–20°/C. below the $T_m$ of the probe for moderate stringency, and in 0.1×SSPE, 0.1% at 10°/C. below the $T_m$ of the probe for high stringency conditions) (see Sambrook et al., Molecular Cloning: A Laboratory Manual, 2nd Ed., Cold Spring Harbor Laboratory Press, NY, 1989); or (c) nucleic acid sequences are degenerate as a result of the genetic code to the nucleic acid sequences defined in (a) or (b). Furthermore, although nucleic acid molecules are primarily referred to herein, as should be evident to one of skill in the art given the disclosure provided herein, a wide variety of related nucleic acid molecules may also be utilized in various embodiments described herein, including for example, RNA, nucleic acid analogues, as well as chimeric nucleic acid molecules which may be composed of more than one type of nucleic acid.

Within another aspect of the present invention, probes and primers are provided for detecting nucleic acids sequences which encode 799/801NKA. Within one embodiment of the invention, probes are provided which are capable of hybridizing to 799/801NKA nucleic acids (DNA or RNA). For purposes of the present invention, probe, are "capable of hybridizing" to 799/801NKA nucleic acids if they hybridize to SEQ ID NO 5 to 8 under conditions of moderate or high stringency (see the section above concerning nucleic acid molecules, and Sambrook et al., supra); Preferably, the probe may be utilized to hybridize to suitable nucleotide sequences in the presence of 5×SSPE, 0.1% SDS, and 0.1% mg/ml ssDNA at 10–20°/C. below the $T_m$ of the probe. Subsequent washes may be performed in 1×SSPE, 0.1% SDS at 15–20°/C. for conditions of moderate stringency, and in 0.1×SSPE, 0.1% SDS at 10°/C. below the $T_m$ of the probe for conditions of high stringency.

Probes of the present invention may be composed of either deoxyribonucleic acids (DNA) ribonucleic acids (RNA), nucleic acid analogues, or any combination of these, and may be as few as about 12 nucleotides in length, usually about 14 to 18 nucleotides in length, and possibly as large as the entire sequence which encodes 799/801NKA. Selection of probe size is somewhat dependent upon the use of the probe. For example, a long probe used under high stringency conditions is more specific, whereas a oligonucleotide carefully selected from the sequence can detect a structure of special interest.

Probes may be constructed and labeled using techniques which are well known in the art. Shorter probes of, for example, 12 or 14 bases may be generated synthetically. Longer probes of about 75 bases to less than 1,5 kb are preferably generated by, for example, PCR amplification in the presence of labeled precursors such as 32p-dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells (see Sambrook et al., supra).

Probes may be labeled by a variety of markers, including, for example, radioactive markers, fluorescent markers, enzymatic markers, and chromogenic markers The use of 32p is particularly preferred for marking or labeling a particular probe.

As noted above, nucleic acid probes of the present invention may be utilized to detect the presence of 799/801NKA nucleic acid molecules within a sample. However, if such nucleic acids molecules are present in only a limited number, then it may be beneficial to amplify the relevant sequence such that it may be more readily detected or obtained.

A variety of methods may be utilized in order to amplify a selected sequence, including, for example, RNA amplification (see Lizardi et al., Bio/Technology 6:1197–1202, 1988; Kramer et al., Nature 339:401–402, 1989; Lomeli et al., Clinical Chem. 35(91) 1826–1831, 1989; U.S. Pat. No. 4,786,600), and nucleic acid amplification utilizing Polymerase Chain Reaction ("PCR") (see U.S. Pat. Nos. 4,683, 195, 4,683,202, and 4,800,159) (see also U S. Pat. Nos. 4,876,187, and 5,011,769, which describe an alternative detection/amplification system comprising the use of scissile linkages).

Within a particularly preferred embodiment, PCR amplilication is utilized to detect or obtain 799/801NKA nucleic acids. Briefly, as described in greater detail below, a nucleic acid sample is denatured at 95° C. in order to generate single stranded nucleic acid. Specific primers, as discussed below, are then annealed at 37° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence. A nucleic acid sequence probe is necessary for the detection for the presence of the 799/801NKA, comprising at least XYZCCCXYZ, preferably TCCAXYZCCCXYZGGCACCG, derived from SEQ ID NO 5–7 where XYZ is TGT or CTG and at least one them is TGT and where this nucleic acid sequence probe has preferably a length of 9–100 nucleotides. A method for detecting the 799/801NKA in a cell, would comprise the steps of
   a) rendering the DNA of the cell available for detection according to generally known methods;
   b) carrying out a PCR detection using the probe above,
   c) detecting the presence of amplification products formed in step b) by generally known methods.

A kit for detecting the presence of the 799/801NKA in a cell must comprise a nucleic acid sequence probe mentioned above Primers for the amplification of a certain sequence should be selected from sequences which are highly specific and form stable duplexes with the target sequence. The primers should also be non-complementary, especially at the 3' end, should not form dimers with themselves or other primers, and should not form secondary structures or duplexes with other regions of nucleic acid. In general, primers of about 18 to 20 nucleotides are preferred, and may be easily synthesized using techniques well known in the art.

In another aspect, the present invention relates to vectors and host cells comprising the above mentioned nucleic acid sequences. The above described nucleic acid molecules which encode 799/801NKA (or portions thereof) may be readily introduced into a wide variety of host cells. Representative examples of such host cells include plant cells, eukaryotic cells, and prokaryotic cells. Within preferred embodiments, the nucleic acid molecules or proteins are introduced into cells from a vertebrate or warm-blooded animal, such as a human, macaque, dog, cow, horse, pig, sheep, rat, hamster, mouse, or a fish, or any hybrid thereof.

The nucleic acid molecules (or vectors) may be introduced into host cells by a wide variety of mechanisms, including for example calcium phosphate-mediated transfection (Wigler et al., Cell 14:725, 1978), lipofection; gene gun (Corsaro and Pearson, Somatic Cell Gen. 1:603, 1911; Graham and Van der Eb, Virology 52:456, 1973), electroporation (Neumann et al,. EMBO J. 1:841–845, 1982), retroviral, adenoviral, protoplast fusion-mediated transfection or DEAE-dextran mediated transfection (Ausubel et al., (eds.), Current Protocols in Molecular Biogly, John Wiley and Sons, Inc., NY, N.Y., 1987)

The nucleic acid molecules, antibodies, and proteins of the present invention may be labeled or conjugatad (either through covalent or non-covalent means, to a variety of labels or other molecules, including for example, fluorescent markers, enzyme markers, toxic molecules, molecules which are nontoxic but which become toxic upon exposure to a second compound, and radionuclides.

Representative examples of fluorescent labels suitable for use within the present invention include, for example, Fluorescein Isothiocyanate (FITC), Rodamine, Texas Red, Luciferase and Phycoertyrin (PE). Particularly preferred for use in flow cytometry is FITC which may be conjugated to purified antibody according to the method of Keltkamp in "Conjugation of Fluorescein Isothiocyanate to Antibodies I. Experiments on the Conditions of Conjugation," Immunology 18 865–873, 1970. (See also Keltkamp, "Conjugation of Fluoresscein [sothiocyanate to Antibodies. II. A Reproducible Method," Immunology 18:875–881, 1970; and Goding, "Conjugation of Antibodies with Fluorochromes: Modification to the Standard Methods," J. Immunol. Methods 13:215–226, 1970). For histochemical staining, HRP, which is preferred, may be conjugated to the purified antibody according to the method of Nakane and Kawaoi ("Peroxidase-Labeled Antibody: A New Method of Conjugaion,"]. Histochem. Cytochem. 22:1084–1091, 1974; see also, Tijssen and Kurstak, "Highly Efficient and Simple Methods for Preparation of Peroxidase and Active Peroxidase Antibody Conjugates for Enzyme Immunoassays," Anal. Biochem. 136;451–457, 1984).

Representative examples of enzyme markers or labels include alkaline phosphatase, horse radish peroxidase, and β-galactosidase. Representative examples of toxic molecules include ricin, abrin, diphtheria toxin, cholera toxin, gelonin, pokeweed antiviral proteein, tritin, Shigella toxin, and Pseudomonas exotoxin A. Representative examples of molecules which are nontoxic, but which become toxic upon exposure to a second compound include thymidine kinases such as HSVTK and VZVTK. Representative examples of radionuclides include Cu-64, Ga-67, CTa-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212.

As will be evident to one of skill in the art given the disclosure provided herein the above described nucleic acid molecules, antibodies, proteins and peptides may also be labeled with other molecules such as colloidal gold, as well either member of a high affinity binding pair (e.g., avidin-biotin).

As noted above, the present invention also provides a variety of phamiaceutical compositions, comprising eucaryotic cells transformed with genes encoding 799/801/NKA, along with a pharmaceutically or physiologically acceptable carrier, excipients or diluents. Generally, such carriers should be nontoxic, to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Such compositions may find use in gene therapy applications.

In addition, the pharmaceutical compositions of the present invention may be prepared for administration by a variety of different routes, including for example intraarticularly, intracranially, intradermally, intramuscularly, intraocularly, intraperitoneally, intrathecally, intravenously, subcutaneously or even directly into a tumor (for example, by stereotaxic injection). In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e,g., water, saline or PBS) which may be necessary to reconstitute the pharmaceutical composition.

As previously mentioned, effective amounts of the protein or fragments or variants thereof can be used as active ingredients in pharmaceutical compositions possibly together with pharmaceutically acceptable excipients. Examples of suitable excipients are mannitol, lactose, starch, cellulose, glucose, etc., only to mention a few. The examples given of the adjuvant and the excipients are not to be regarded as limiting the invention.

Accordingly, the invention is useful in, among all, following fields:

Genetical: To select gene transfected cells for purifying and multiplying specific cell populations in the field of gene-therapy on humans and animals and also for screening succesful in the area of transfections of cells in cell cultures. This gives the possibility, after the selection is made, to evaluate the efficiency of the transfection/gene therapy by method used. There is also a possibilty to store purified transfected cells for further use (e.g. at −70° C. in liquid nitrogen). This procedure can be repeated to obtain a suitable amount of cells needed for therapy.

Physiological: The mutation/mutations in the protein preferrably (Na,K)-ATPase and its effects can be used in cell cultures and in transgenetical animals in studies on a cellular, organ and fullbody level in connection with the use of effects of cardiac glycosides ( e.g. digitalis).

In this system, a gene is used which is already expressed in all mammalian cells and which is essential for the survival of the cell. Earlier studies have shown that the activity of this enzyme can be influenced by the chemical substance ouabain (a cardiac glycoside) which is closely related to digitalis. The sensitivity for this influence depends on the structure of the enzyme and through mutations of the enzyme it can be altered (Lingrel J. B. Jour. Biol. Chem. 1994 pp. 10659–19662; Palais M., Jour. Biol. Chem., 1996, pp. 14176–14182; Burns, E:L., Jour. Biol. Chem., 1996 pp15879–15883). In these studies the gene in lamb was used and it was shown that different mutations gave different results.

Here a specific mutation was made in the rat NKA alpha 1 subunit where the amino acid leucin-799 was altered to the amino acid cysteine in the same position in the geine coding for the alphal-subunit of (Na,K)ATPase (NKA) in the rat (FIG. 1) which unexpectedly resulted in an enzyme with an almost complete resistance to ouabain. Also experiments using the same NKA alpha 1 subunit but where the mutation had been done in position 801 instead of 799 from leucine to cysteine, result in the same effect as the one above. Cantley et al (Jour. Biol. Chem. 1994 pp 15358–61) have shown a mutation in murine and Thuman NKA alpha 1-subunit and its importance for oubain resistance. They have reported about cells with an $IC_{50}$ for ouabain of approximately 5 mM.

NKA is an integral membrane protein found in the cells of all higher eukaryotes and is responsible for translocating sodium and potassium ions across the cell membrane utilizing ATP as the driving force. The NKA is member of the P-type class of ATPases which includes the sarcoplasmic reticulum and plasma membrane C2+-ATPases and the H+,K+-ATPases found in stomach and colon, in addition to several prokaryotic transport enzymes (Lingrel J., Jour. Biol. Chem., 1994, pp 19659–19662, hereby incorporated as reference). These enzymes share a similar catalytic cycle that involves a phosphorylated protein intermediate.

The NKA is composed of two subunits in equimolar ratios. These are the alpha-subunit with a molecular mass of approximately 113 kDa and the smaller glycosylated beta-subunit with a protein portion accounting for 35 kDa of the over all molecular mass of 55 kDa. Isoforms exists for both the α (α1, α2 and α3) and β (β1, β2 and β3) subunits. The α1 isoform occurs in most tissues, while the α2 isoform is predominant in skeletal muscle and is also detected in the brain and in the heart. The α3 isoform is limited essentially to neural and cardiac tissue.

Due to the fact that all mammals (in particular humans, chicken, horses, pigs, sheep but also shrimps like Bufus marinus) have approximately the same sequence in this area i.e. 20 amino acids upstream and 20 amino acid downstream from this mutation it is very likely that a similar mutation in these species will render in a similar enzyme with the same characteristics. It is also very likely that if a change of the leucin in position 801 to a cysteine occured together with a change in position 799 from leucine to cysteine an enzyme would be obtained also with similar characteristics as the NKA alpha 1 subunits with only one mutation in either position 799 or 801. However, this specific amino acid substitution is of great importance for the result. The unique and unexpected in this was that we showed that the change of amino acid leucin 799 to cysteine in the rat gene coding for NKA alpha1-subunit gives this drastic change in ouabain sensitivity. At ouabain concentrations up to 2 mM, no significant inhibition of the enzyme could be detected. Also other cardiac glycosides could be thinkable such as: ouabagenin, digitoxin, digitogenin, digoxin, bufalin. The cardiac glycosides could possibly be used in concentrations from 1 nM to 5000 μM, preferably 1 μM to 5000 μM, to separate cells comprising the mutated NKA from cells not comprising the mutated NKA where the cells are exposed to a cardiac glycoside and the surviving cells are recovered.

The very high similarity in amino acid sequence between species and isoforms of this enzyme, in the region of interest, strengthen the possibility that these mutations can be used in several other species and isoforms different from rat Nha+,K+-ATPase alpha 1 subunit. This gives the invention wider fields of availability. It is also very likely that by using the mutated NKA subunit from each species a selection of cells can be done in that particular species by using the NKA subunit in that particular species. This will probably result in the most natural selection system of today.

An example of the amino acid (a a) similarity in this domain (62 aa upstream and 82 aa downstream of the mutations). The similarity (homology) is given as % of rat alpha 1 subunit sequence:

| Human alpha1 | 100% |
| Human alpha3 | 97,2% |
| Horse alpha1 | 99,3% |
| Pig alpha1 | 99,3% |
| Pig alpha3 | 98,6% |
| Chicken alpha1 | 98,6% |

-continued

| Chicken alpha2 | 99,3% |
| Chicken alpha3 | 96,5% |
| Sheep alpha1 | 98,6% |
| Rat alpha2 | 98,6% |
| Rat alpha3 | 96,5% |

These different subunits in a suitable mix would be useful when preparing transgenetic animals with different characteristics.

Earlier the natural gene coding for the NKA alpha1-subunit had been used (Ouabr-vector, see Research Catalogue 1994–1995 from PharMingen page 271) for transfection selection, but this has had limitations due to that its resistance had only been partial and only a few celltypes could be transfected. The NKA alpha 1 subunit here came from rat which only makes it usefull when dealing with rats. This new enzyme (NKA-Leu799Cys; here we call it 799NKA) with a total unsensitivity for ouabain makes this mutated protein and its corresponding gene interesting in several areas both in research and clinically.

The fact that the α1 subunit of NKA is expressed in all types of cells can be used by using the natural genomic areas/regions which controls the transcription activity of the gene. One example of a genetic structure which can be a part of the construction which is intended to be used in the area of gene therapy is the following:

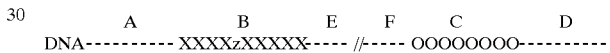

Where A,D,E and F are the natural regulatory genomic structures uppstream and down-stream of the genes, alternatively fundamentally activated regulatory structures, B is a"selection gene" which is a for the cell naturally occuring gene which is expressed in all cells and has one for the cell essential function (in our example 1 subunit of NKA). This gene is mutated so that it has got one or more characteristics altered (not dangerous for the cell) which makes the cell possible to be distinguished from the naturally occuring gene and untransfected cells (in our example (NKA L799C/L801C). Where z represents the mutation in the "selection gene".

and C is the gene which the most important for gene therapy itself.

In U.S. Pat. No. 4,474,893, hereby incorporated as reference, there has been suggested to use hybridomas resistant to ouabain for selection. Ouabain-resistant cells would be able to survive levels of ouabain which kill normal ouabain-sensitive cells. Ouabain-resistance may be used as a selection marker by itself, or in combination with other markers. It is also very likely that by mutating other essential proteins in cells you could acquire a similar possibility to make selection among cells i.e. cells which have received this minor, natural, mutation from ordinary cells. Other essential proteins in the cells are e.g. metabolic enzymes and DNA or RNA polymerases.

An explanation to why this mutation to cysteine in position 799 causes this huge difference when using the NKA in high concentrations of ouabain might be that there is a cys=cys disulfide bridge formed (Kirley, T. L. et, Jour. Biol. Chem 1986, pp 4525–4528). The suggested binding between a cysteine and ouabain could be abolished in view of the invention described in this application due to the formation of the formation of this cyc=cys bridge. This theory shall not however limit the invention in any form.

The invention will now be described in more detail with reference to the accompanying drawing, in which

BRIEF DESCRIPTION OF THE DRAWINGS

The results in FIG. 2 are presented as means of 3 experiments. One can clearly see a "loss of attachment" in untransfected and wild type transfected cells compared to L799C Na+,K+-ATPase transfected cells.

DETAILED DESCRIPTION OF PREFERRED EMBODIMENTS

Figure 1:
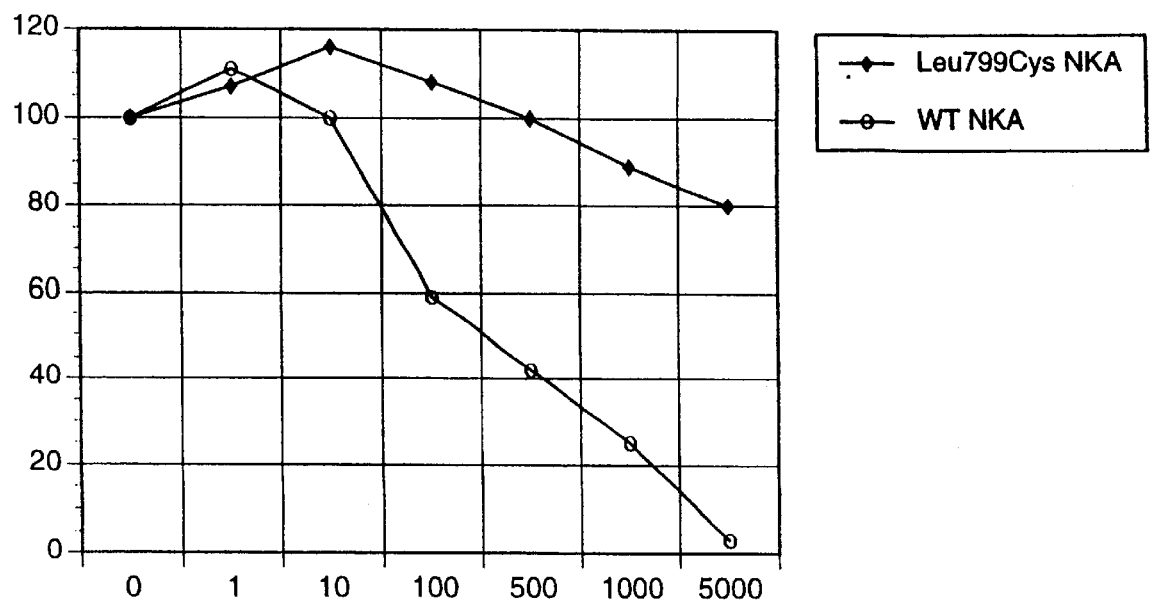
FIG. 1 shows (Na,K)ATPasc activity in percent in comparison with not treated vs ouabain concentration in $\mu$M. The Leu799Cys NKA is a (Na,K)-ATPase where the leucine 799 is mutated to cysteine. WT NKA is natural (Na,K)-ATPase.
Figure 2:
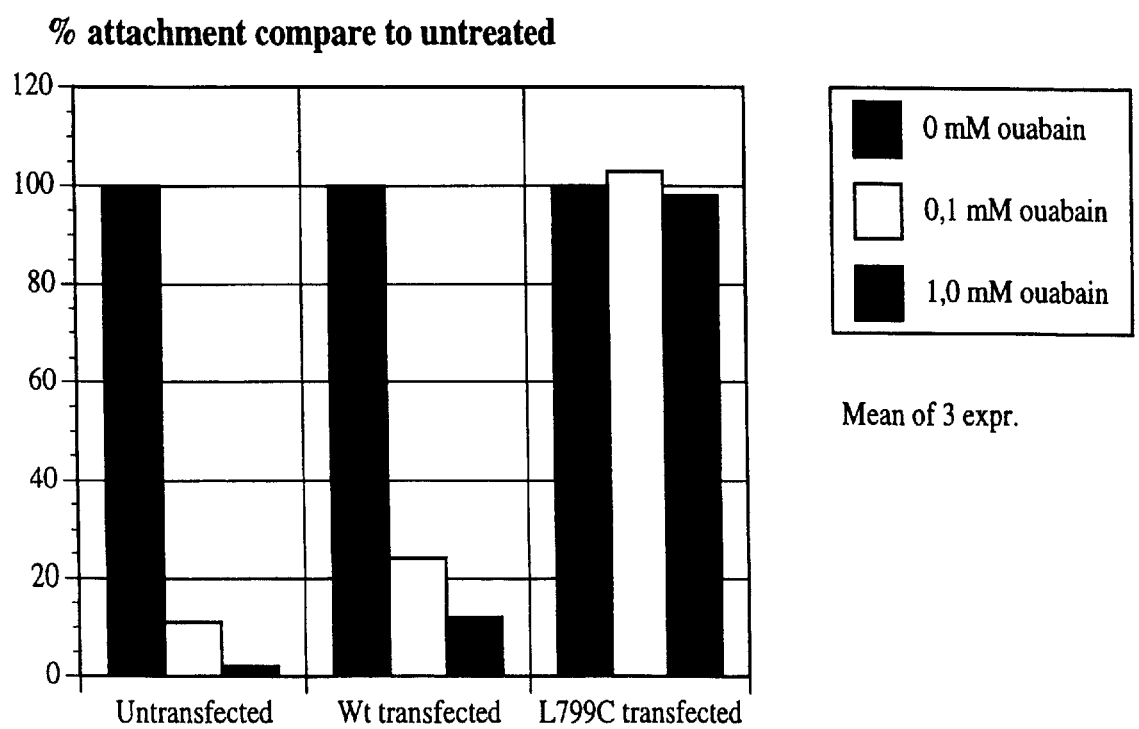
In FIG. 2, the solid bar on the left of each group represents 0 mM ouabain, whereas the solid bar on the right of each group represents 1.0 mM ouabain.

SEQ ID NO:1 relates to a (Na,K)ATPase (NKA) alpha 1 subunit with its leucine 879 (corresponds to 799) mutated to cysteine. SEQ ID NO:2 relates to a (Na,K)ATPase (NKA) alpha 1 subunit with its leucine 881 (corresponds to 801) mutated to cysteine. SEQ ID NO:3 relates to a (Na,K) ATPase (NKA) alpha 1 subunit with its leucine 879 (corresponds to 799) mutated to cysteine and also its leucine 881 (corresponds to 801) mutated to cysteine. SEQ ID NO:4 is natural NKA alpha 1 subunit. SEQ ID 5–8 are the corresponding DNA-sequences to the above mentioned amino acid sequences. NO:1 corresponds to NO:5, NO:2 corresponds to NO:6 , NO:3 corresponds to NO:7 and NO:4 corresponds to NO:8. SEQ ID NO:s 1–4 include an 80 amino acid start peptide and SEQ ID NO:s 5–8 include a 240 nucleic acid long start codon.

The invention will now be further described with reference to the following examples. These examples are only given for the purpose of illustration and are not intended to limit the scope of the invention claimed herein.

EXPERIMENTAL PROCEDURES

MUTAGENESIS

To introduce the mutation leucine 799 to cysteine (L799C) cr leucine 801 to cysteine (L801C) in the rat Na+,K+-ATPase a1 subunit, a cDNA sequence of the gene inserted into a PBS+BlueScript vector was used. And the mutations was introduced using a polymerase chain reaction mutation strategy (Pfu DNA polymerase from Stratagene, La Jolla, Calif. To produce the fragments needed to create each mutation, PCR was carried out with the following primer pairs: to create the L799C mutation:

5'-ATGATTGACCCTCCTCGAGCTGCT-'3(SEQ ID NO:13)5'-AATAAATATCAAGAAGGGGGTGAT-'3 (SEQ ID NO:14)

5'-GGCCTGGATCATACCOATCTGT-'3(SEQ ID NO:15)5'-ATTGCAAA(ATTCCATGTCCCCTGG-'3, (SEQ ID NO:16) to create the L801C mutation.

5'-ATGATTGACCCTCCTCGAGCTGCT-'3 5-GTTTGCAATAATAAATATCAAGAAGGG-'3' (SEQ ID NO:17)-GGCCTGGATCATACCGATCTGT-'3

5'-ATTCCACTGCCCTGTGGCACCGTGA-'3(SEQ ID NO:18). The following PCR reaction cycles were used: 96° C. for 3 min followed by 30 cycles of 57° C. for 30 sec, 72° C. for 1 min and 95° C. for 20 sec, and finally 72° C. for 5 min. The fragments were subjected to a polynucleotide kinase reaction (Boehringer Mannheim, Germany) for 30 min at 37° C. and then ligated with the ligase chain reaction (LCR) (Pfu DNA ligase, Stratagene, La Jolla, Calif.) with wild type rat Na+,K4-ATPase a1 cDNA as a template. The following LCR reaction cycles were used: 96° C. for 2 min and 60° C. for 2 min followed by 30 cycles of 96° C. for 20 sec and 60° C. for 20 sec.

The mutated fragments was purified by agarose gel electropboiesis, digested with Bcl 1 and Eco 47 (New England Biolabs Inc. USA) restriction enzymes and substituted for the wild type fragment. Each complete clone was sequenced with an Applied Biosystems Taq Dye Deoxy Terminator Cycle Sequencing Kit in a Perkin-Elmer Cetus DNA Thermal Cycler 9600 to confirm the mutation and exclude other mutations.

Transfection:

Wild type and the mutant Na+,K+-ATPase a1 were subcloned in a CMV- or adenovirus promotor containing mammalian expression vector and stabled transfected into COS7 (monkey), LLC-PK1 (pig) and MDCK (dog) cells using the (calcium Phosphate method (described by Okayama, H., and Chen, C. (1991) in Gene transfer and expression protocols. (Murray E J, ed) pp 15–21, Humana Press, New Jersey). Cells were grown in Dulbecco's modified Eagle's medium (DMEM) supplemented with 10% fetal-calf serum arid 50% penicillin/streptomycin in 37° C. humified air with 5.3 % $CO_2$. The cells, which are derived from different spices than rat, express a relative high ouabain-sensitive Na+,K+-ATPase. Selection of transfected clones was achieved as described (Fisone, G., Cheng, S., Nairn, A., Czeriik, A., Hemnungs, H., Hvvg, J., Bertorello, A., Kaiser, R., Bergman, T., Jvrnvall, H., Aperia, A. and Greengard, P. (1994)J. Biol. Chem. 269, 9368–9373, Vilsen, B. FEBS Letters (1992) 314(3) 301–307 and Vilsen, B. Biochemistry (1993) 32(48): 13340–13349). Briefly, cells were grown in 10 or up to 500 $\mu$M ouabain for 3–4 weeks, and the medium was changed every third day. Untransfected cells died within 2–3 days in ouabain medium, while cells expressing the relatively ouabain-insensitive wild type or mutant rat Na+, K+-ATPase a1 subunit survived. Following this ouabain selection procedure, several hundred single clones with approximately the same growth rate were pooled and replated in DMEM containing 10 or 500 $\mu$M ouabain. We selected clones of cells, expressing wild type and mutant Na+,K+-ATPase, that had similar levels of transfected Na+, K+-ATPase activity. The abundance of Na+,K+-ATPase, as determined by immunoblotting, was also within the same range in both cell types. In pilot studies we could clearly distinguish between ouabain-sensitive (endogenous) and ouabain-insensitive (transfected) Na+,K+-ATPase populations that were completely inhibited (the wild type enzyme) by ouabain concentrations of $10^{-5}$ M and $5 \times 10^{-3}$ M, respectively. Approximately 60% of Na+,K+-ATPase was resistant to $10^{-5}$ M ouabain and was considered to be rat wild type or mutated Na+,K+-ATPase. Furthermore, the expression of wild type and mutant Na+,K+-ATPase mRNA was in each protocol verified by RT-PCR with RNase free DNase (Pharmacia Biotech, Sweden) treated total RNA.

ATP hydrolysis:

Cells expressing wild type and mutant Na+,K+-ATPase were seeded ($3.0 \times 10^5$ cells/well) in 30 mm diameter wells and grown to confluence. Cells were lysed by treatment with 1 mM Tris-HCl pH 7.5 on ice for 15 min and a crude membrane fraction was prepared as described (Horiuchi, A., Takeyasu, K., Mouradian, M., Jose, P and Felder, R (1993)

Mol. Phamiacol. 43, 281–285). The membrane fraction was frozer, in aliquots and stored over-night at −70° C. Na+,K+-ATPase-dependent ATP hydrolysis was measured in triplicate as described (Fisone, G., Cheng, S., Nairn, A., Czernik, A., Heinnings, H., Hvvg, J., Bertorello, A., Kaiser, R., Bergman, T., Jvrnall, H., Aperia, A. and Greengard, P. (1994)J. Biol. Chem. 269, 9368–9373, hereby incorporated as reference). Transfected Na+,K+-ATPase activity was determined as the difference between ATPase activity at $10^{-5}$ M and at stepwise increasing concentrations of ouabain.

These experimental procedures gave these results in three different examples:

EXAMPLE 1

After the mutation (leucin 799 to cysteine) in the (Na,K)-ATPase had been created it was transfected to a mammalian cell line (COS-7). The activity of the normal and the mutated enzyme was studied (see FIG. 1). You can see that the murated enzyme keeps its activity at almost 100%, while the activity of the natural enzyme is inhibited 85–90% at a concentration of 2 mM ouabain.

EXAMPLE 2

A cell surviving study was done where the cells transfected with the mutated enzyme survived a longtime treatment with 500 μM ouabain while the cells transfected with the natural enzyme died at a concentration of 500 μM.

EXAMPLE 3

LLC-PK1 (cells from pig kidney) and MDCK (cells from dog kidney) have also been transfected and survival studies have shown that these cell types also survive, multiply and keep their natural exterior at ouabain concentrations up to 500 μM.

It is generally accepted that the LLC-PK 1 cells have a tendency to differentiate when the cell population is grown to confluence and the cells form circular configurations with transporting properties similar to epithelial cells. Transfection of the mutated (L799C and/or L801C) rat Na+,K+-ATPase alphal subunit into the LLC-PK1 cells did not seem to alter these cells growing and morphological characteristics, in as high as $500 \times 10^{-6}$ M ouabain. Transfection of the COS 7 and MDCK cell lines did not affect these cells growing and morphology as in the case for the LLC-PK1 cells.

Untransfected cells died within a few days in $1-50 \times 10^{-6}$ M ouabain, wild type transfected cells died within a few days in a $500 \times 10^{-6}$ M ouabain while mutant transfected cells survived as high as at least $1 \times 10^{-3}$ M ouabain.

EXAMPLE 4

Cell Attachment

Cell attachment on fibronectin coted substrates was assayed in microtiterwells (Costar). All wells were preincubated over night at 4° C. with 5 microg/ml concentration of fibronectin. Before adding cells, each well was preincubated with 1% BSA for 30 min in 37° C. and later washed with serum free DMEM. Untransfected COS-7 cells and COS-7 cells expressing wild type or L799C Na+,K+-ATPase were grown in a 3 microCi/ml H3-thymidine containing medium supplemented with 10% fetal calf serum and harvested after approximately 72 hours at 60–80% confluence. Approximately 25,000 cells /wells were seeded in serum free DMEM. Cells were first incubated 15 min with different concentrations of oubain and then allowed to attach to fibronectin (5 μg/ml) coated substrates during 30 min of incubation in 37° C. and later washed with serum free DMEM. Radioactivity was measured in a Wallac Scintillation counter. Results are presented as % remaining radioactivity compared to untreated.

Results cell Attachment

This system is based upon differences in cell attachment between transfected and untransfected cells when they are exposed to oubain. Since we here can show that an inhibition of Na+,K+-ATPase activity lead to an concomitant inhibition of cell attachment this can be used to select transfected cells, ready to be used in different applications, within a few hours instead of several weeks. This can speed up the procedure several fold. During selection with different concentrations of oubain (i.e. inhibition of Nat-, K+-ATPase), cell attachment was decreased dose dependent in untransfected cells but no change in attachment was noted in transfected cells. When complete inhibition of Na+,K+ ATPase was achieved almost no attachment was seen. The effect on attachment was seen within minutes. This procedure could be repeated to obtain a 100% selection efficiency within hours.

What is claimed is:

1. A nucleic acid sequence encoding an oubain-resistant (Na, K)-ATPase comprising SEQ ID NO: 9 wherein Xaa at position 17 is Leu, Xaa at position 18 is Cys, and Xaa at at least one of positions 9 and 11 is Cys.

2. A sequence according to claim 1, wherein said oubain-resistant (Na, K)-ATPase comprises at least one of the following three amino acid sequences: IFIIANIPCPLGTVTILCID, IFIIANIPLPCGTVTILCID, or IFIIANIPCPCGTVTILCID (SEQ ID NOS: 10–12).

3. A sequence according to claim 1, wherein said oubain-resistant (Na, K)-ATPase has an amino acid sequence according to any one of SEQ ID NO: 1, SEQ ID NO: 2 and SEQ ID NO: 3.

4. A vector comprising the nucleic acid of claim 1.

5. A cell comprising a vector according to claim 4.

6. A nucleic acid molecule comprising nucleic sequence according to claim 1, for medical use.

7. A vector for use in gene therapy comprising a nucleic acid molecule according to claim 1, together with another heterologous nucleic acid sequence.

* * * * *